United States Patent
Elenbaas et al.

(10) Patent No.: US 7,422,899 B2
(45) Date of Patent: Sep. 9, 2008

(54) ANTIBODIES TO THE HUMAN PROLACTIN RECEPTOR

(75) Inventors: Brian Elenbaas, Melrose, MA (US);
Matthew B Jarpe, Quincy, MA (US);
Steven D. Miklasz, Upton, MA (US);
Stephen E. Fawell, Framingham, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 11/538,635

(22) Filed: Oct. 4, 2006

(65) Prior Publication Data

US 2007/0269438 A1 Nov. 22, 2007

Related U.S. Application Data

(60) Provisional application No. 60/724,054, filed on Oct. 5, 2005.

(51) Int. Cl.
*C12N 5/00* (2006.01)
(52) U.S. Cl. .................. 435/346; 435/332; 530/350; 530/387.1; 530/387.3; 530/391.3
(58) Field of Classification Search .............. 435/346, 435/332; 530/350, 387.1, 387.3, 391.3
See application file for complete search history.

(56) References Cited

U.S. PATENT DOCUMENTS

| | | | |
|---|---|---|---|
| 4,474,893 | A | 10/1984 | Reading |
| 4,714,681 | A | 12/1987 | Reading |
| 4,816,567 | A | 3/1989 | Cabilly et al. |
| 4,925,648 | A | 5/1990 | Hansen et al. |
| 5,229,275 | A | 7/1993 | Goroff |
| 5,567,610 | A | 10/1996 | Borrebaeck et al. |
| 5,573,920 | A | 11/1996 | Randle |
| 5,585,089 | A | 12/1996 | Queen et al. |
| 5,641,870 | A | 6/1997 | Rinderknecht et al. |
| 5,648,237 | A | 7/1997 | Carter |
| 5,693,761 | A | 12/1997 | Queen et al. |
| 5,693,762 | A | 12/1997 | Queen et al. |
| 5,731,168 | A | 3/1998 | Carter et al. |
| 5,739,277 | A | 4/1998 | Presta et al. |
| 5,789,199 | A | 8/1998 | Joly et al. |
| 5,807,706 | A | 9/1998 | Carter et al. |
| 5,821,333 | A | 10/1998 | Carter et al. |
| 5,840,523 | A | 11/1998 | Simmons et al. |
| 5,869,046 | A | 2/1999 | Presta et al. |
| 5,939,598 | A | 8/1999 | Kucherlapati et al. |
| 6,180,370 | B1 | 1/2001 | Queen et al. |
| 2002/0155537 | A1 | 10/2002 | Carter et al. |
| 2003/0020734 | A1 | 1/2003 | Yin et al. |
| 2004/0023341 | A1 | 2/2004 | Xu et al. |
| 2005/0036942 | A1 | 2/2005 | Devaux et al. |

FOREIGN PATENT DOCUMENTS

| | | |
|---|---|---|
| WO | WO 91/00360 | 1/1991 |
| WO | WO 92/05793 | 4/1992 |
| WO | WO 92/08802 | 5/1992 |
| WO | WO 93/17715 | 9/1993 |
| WO | WO 00/44788 | 8/2000 |
| WO | WO 02/096948 | 12/2002 |

OTHER PUBLICATIONS

Banerjee et al (Int. J. Can., 55:712-721, 1993).*
Hand et al (Can. Res., 43:728-735, 1983).*
Ben-Jonathan et al., "Prolactin as an autocrine/paracrine growth factor in human cancer." Trends Endocrinol. Metal. 13:245-250 (2002).
Bernichtein et al., "Development of Pure Prolactin Receptor Antagonists." J. of Biol. Chem. 278(38):35988-35999(2003).
Carter et al., "High Level *Escherichia coli* Expression and Production of a Bivalent Humanized Antibody Fragment." Bio/Technology 10:163-167 (1992)
Carter et al., "Humanization of an anit-p185[Her2] antibody for human cancer therapy." Proc. Natl. Acad. Sci. USA 89:4285 (1992).
Chen et al., "A Human Prolactin Antagonist, hPRL-G129R, Inhibits Breast Cancer Cell Proliferation through Induction of Apoptosis." Clin. Cancer Res. 5:3583-3593 (1999).
Chen et al., "In vivo studies of the anti-tumor effects of a human prolactin agtagonist, hPRL-G129R." Int. J. Oncol. 20:813-818 (2002).
Chothia and Lesk "Canonical Structures for the Hypervariable Regions of Immunoglobulins." J. Mol. Biol., 196:901-917 (1987).
Clackson et al., "Making antibody fragments using phage display libraries." Nature, 352:624-628 (1991).
Clevenger et al., "Expression of Prolactin and Prolactin Receptor in Human Breast Carcinoma." Am. J. of Path. 146(3):695-705 (1995).
Clevenger et al., "The Role of Prolactin in Mammary Carcinoma." Endocrine Reviews, 24(1):1-27 (2003).
Clevenger et al., "Prolactin receptor signal transduction in cells of the immune system." J Endocrinol 157, 187-197 (1998).
Evan et al., "Isolation of Monoclonal Antibodies Specific for Human c-myc Proto-Oncogene Product." Molecular and Cellular Biology, 5:3610-3616 (1985).
Field et al., "Purification of a RAS-Responsive Andenylyl Cyplase Complex from Saccharomyces serevisiae by Use of an Epitope Addition Method." Mol. Cell. Biol., 8:2159-2165 (1988).

(Continued)

*Primary Examiner*—Stephen L. Rawlings
*Assistant Examiner*—Brad Duffy
(74) *Attorney, Agent, or Firm*—Fish & Richardson P.C.

(57) ABSTRACT

This invention provides antibodies to the prolactin receptor, particularly the human prolactin receptor. Preferred antibodies are capable of blocking prolactin binding to the prolactin receptor, inhibiting signaling through the prolactin receptor, and/or inhibiting proliferation of cancer cells induced by prolactin. Also provided are nucleic acids encoding the antibodies, vectors and host cells comprising the nucleic acids, and uses of the antibodies and nucleic acids.

13 Claims, 7 Drawing Sheets

OTHER PUBLICATIONS

Fraker et al., "Protein and Cell Membrane Iodinations With a Sparingly Soluble Chloroamide, 1,3,4,6-Tetrachloro-3a,6a-Diphenylglycoluril." Biochem. Biophys. Res. Commun. 80:49-57(1978).

Fuh et al., "Prolactin Receptor Antagonists that Inhibit the Growth of Breast Cancer Cell Lines." J. Biol. Chem. 270(22):13133-13137 (1995).

Gazzano-Santoro et al., "A non-radioactive complement-dependent cytotoxicity assay for anti-CD20 monoclonal antibody." J. Immunol. Methods 202:163-171 (1996).

Ginsburg et al., "Prolactin synthesis and secretion by human breast cancer cells." Cance Res. 55:2591-2595 (1995).

Goffin et al., "Prolactin:The New Biology of an Old Hormone." Annu. Rev. Physiol. 64:47-67 (2002).

Goffin et al., "The Prolactin/Growth Hormone Receptor Family: Structure/Function Relationships." J. Mammary Gland Biol. And Neoplasia 2(1):7-17 (1997).

Hamers Casterman et al., "Naturally occurring antibodies devoid of light chains." Nature 363:446 448 (1993).

Hankinson et al., "Plasma Prolactin Levels and Subsequent Risk of Breast Cancer in Postmenopausal Women." J. Natl. Cancer Inst. 91(7):629-34 (1999).

Haspel et al., "System for Cleavable Fc Fusion Proteins Using Tobacco Etch Virus (TEF) Protease." Biotechniques 30(1): 60-66 (2001).

Hopp et al., "A Short Polypeptide Marker Sequence Useful for Recombinant Protein Identification and Purification." BioTechnology, 6:1204-1210 (1988).

Jones et al., "Replacing the complementarity-determining regions in a human antibody with those from a mouse." Nature, 321:522-525 (1986).

Kohler et al., "Continuous cultures of fused cells secreting antibody of predefined specificity." Nature, 256:495-497 (1975).

Kostelny et al., "Formation of a Bispecific Antibody by the Use of Leucine Zippers." J. Immunol. 148:1547-1553 (1992).

Llovera et al., "Involvement of prolactin in breast cancer: redefining the molecular targets." Experimental Geronotology, Elsevier, 35:41-51 (2000).

Lutz-Freyermuth et al., "Quantitative determination that one of the two potential RNA-binding domains of the A protein component of the U1 small nuclear ribonucleoprotein complex binds with the high affinity to stem-loop II of U1 RNA." Proc. Natl. Acad. Sci. USA, 87:6393-6397 (1990).

Marks et al., "By-Passing Immunization: Building High Affinity Human Antibodies by Chain Shuffling." Bio/Technology, 10:779-783 (1992).

Marks et al., "By-passing Immunization Human Antibodies from V-gene Libraries Displayed on Phage." J. Mol. Biol., 222:581-597 (1991).

Martin et al., "GAP Domains Responsible for Ras p21-Dependent Inhibition of Muscarinic Atrail K+ Channel Currents." Science, 255:192-194 (1992).

McCafferty et al., "Phage Antibodies: filamentous phase displaying antibody variable domain." Nature, 348:552-554 (1990).

Millstein et al., "Hybrid hybridomas and their use in immunohistochemistry." Nature 305:537-539 (1983).

Paborsky et al., "Mammalian cell transient expression of tissue factor for the production of antigen." Protein Engineering, 3(6):547-553 (1990).

Pellegrini et al., Expression of Prolactin and Its Receptor in Human Lymphoid Cells. Mol Endocrinol 6, 1023-1031 (1992).

Perks et al., "Prolactin acts as a potent survival factor for human breast cancer cell lines." Br. J. Cancer 91:305-311 (2004).

Presta et al., "Humanization of an Antibody Directed Against IgE." J. Immunol. 151:2623-2632 (1993).

Reichmann et al., "Reshaping human antibodies for therapy." Nature, 332:323-327 (1988).

Robbins and Angell, Basic Pathology, 2d Ed., W.B. Saunders Co., Philadelphia, pp. 68-79 (1976).

Roux et al., "Comparisons of the Ability of Human IgG3 Hinge Mutants, IgM, IgE, and IgA2, Form Small Immune Complexes:A role for Flexibility and Geometry." J. Immunol. 161:4083-4090 (1998).

Sims et al., "A Humanized CD18 Antibody Can Block Function without Cell Destruction." J. Immunol. 151:2296-2308 (1993).

Skinner et al., "Use of the Glu-Glu-Phe C-terminal Epitope for Rapid Purification of the Catalytic Domain of Normal and Mutant ras GTPase-activating Proteins." J. Biol. Chem., 266:15163-15166 (1991).

Stevenson et al. "A chimeric antibody with dual Fc regions (bisFabFc) prepared by manipulations at the IgG hinge." Anti-Cancer Drug Design 3:219-230 (1989).

Tan et al., "Influence of the hinge region on complement activation, C1q binding, and segmental flexibility in chimeric human immunoglobulins." Proc. Natl. Acad. Sci. USA 87:162-166 (1990).

Tutt et al., "Trispecific F(ab')$^3$ Derivatives That Use Cooperative Signaling Via the TCR/CD3 Complex and CD2 To Activate and Redirect Resting Cytotoxic T Cells," J. Immunol. 147:60-69 (1991).

van Dijk et al., "Human antibodies as next generation therapeutics." Curr Opin Chem Biol. 5(4):368-74 (2001).

Verhoeyen et al., "Reshaping Human Antibodies: Grafting an Antilysozyme Activity." Science, 239:1534-1536 (1988).

Vonderhaar, B.K., "Prolactin involvement in breast cancer." Endocrine-Related Cancer 6:389-404 (1999).

Vonderhaar, B.K., "Prolactin: The Forgotten Hormone of Human Breast Cancer." Pharmacol. Ther. 79(2):169-178 (1998).

Waterhouse et al., "Combinatorial infection and in vivo recombination: a strategy for making large phage antibody repertoires." Nuc. Acids. Res., 21:2265-2266 (1993).

Wennbo et al., "The role of prolactin and growth hormone in breast cancer." Oncogene 19:1072-1076 (2000).

Wolff et al., "Monoclonal Antibody Homodimers: Enhanced Antitumor Activity in Nude Mice." Cancer Research 53:2560-2565 (1993).

\* cited by examiner

Figure 1. Amino acid sequence of PRLR-Fc fusion protein used to immunize mice and screen for antibodies.

(N-terminus) - Q L P P G K P E I F K C R S P N K E T F T C W W R P
G T D G G L P T N Y S L T Y H R E G E T L M H E C P D Y I T G
G P N S C H F G K Q Y T S M W R T Y I M M V N A T N Q M G S
S F S D E L Y V D V T Y I V Q P D P P L E L A V E V K Q P E D
R K P Y L W I K W S P P T L I D L K T G W F T L L Y E I R L K
P E K A A E W E I H F A G Q Q T E F K I L S L H P G Q K Y L V
Q V R C K P D H G Y W S A W S P A T F I Q I P S D F T M N D T
T V W <u>E N L Y F Q G</u> V D K T H T C P P C P A P E L L G G P S V
F L F P P K P K D T L M I S R T P E V T C V V V D V S H E D P E
V K F N W Y V D G V E V H N A K T K P R E E Q Y N S T Y R V V
S V L T V L H Q D W L N G K E Y K C K V S N K A L P A P I E K
T I S K A K G Q P R E P Q V Y T L P P S R D E L T K N Q V S L
T C L V K G F Y P S D I A V E W E S N G Q P E N N Y K T T P P
V L D S D G S F F L Y S K L T V D K S R W Q Q G N V F S C S V
M H E A L H N H Y T Q K S L S L S P G – (C-terminus)

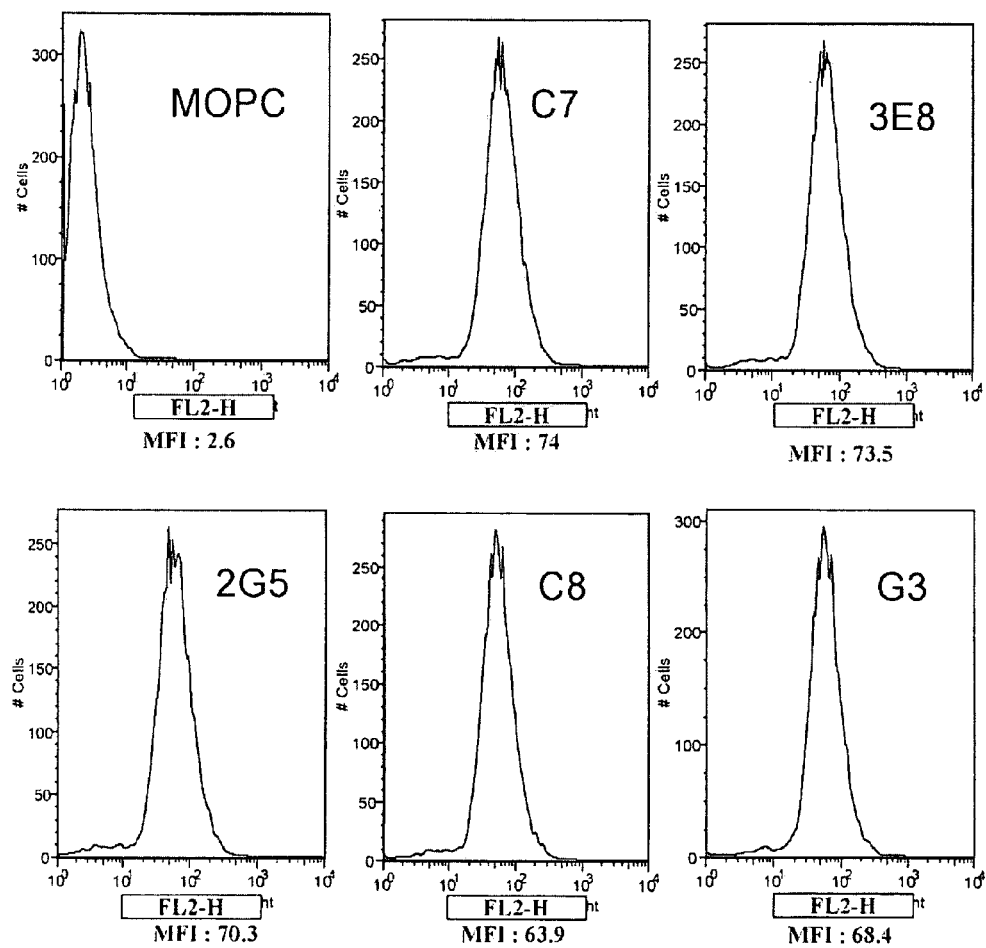
Figure 2. FACS showing binding of mAbs to T-47D and MCF-7 breast cancer cell lines
A. T-47D

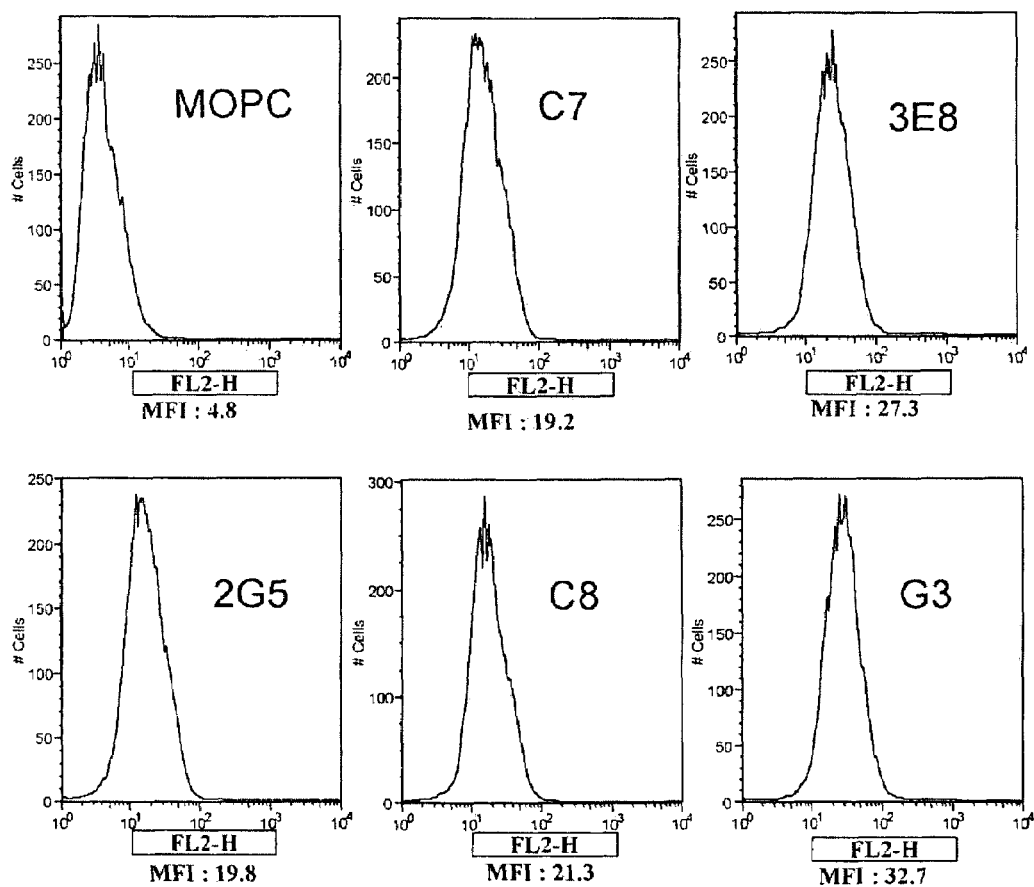
Figure 2. FACS showing binding of mAbs to T-47D and MCF-7 breast cancer cell lines
B. MCF-7

Figure 3. FACS analysis demonstrates that PRLR mAbs are specific to human PRLR.
A. FACS on 293T-human PRLR cells
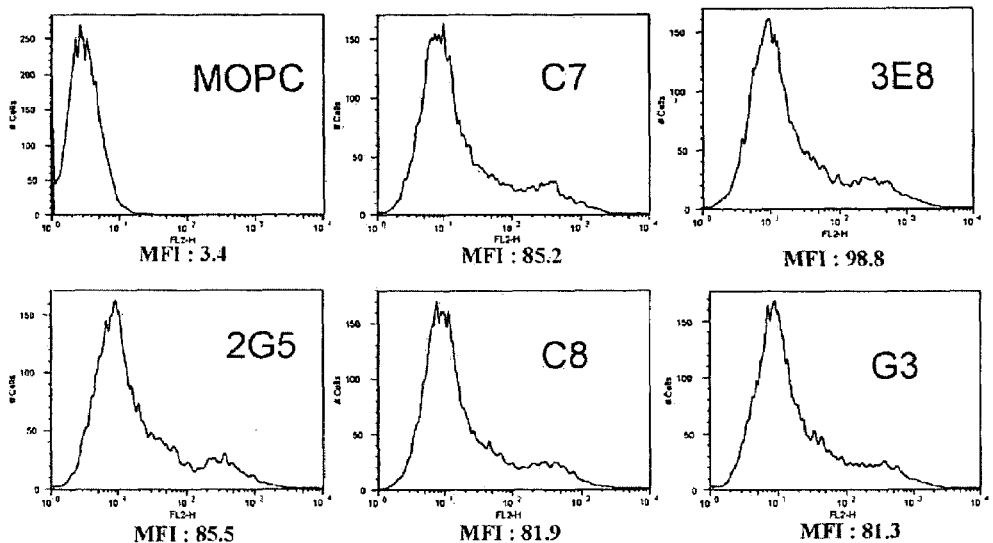
B. FACS on 293T-mouse PRLR cells
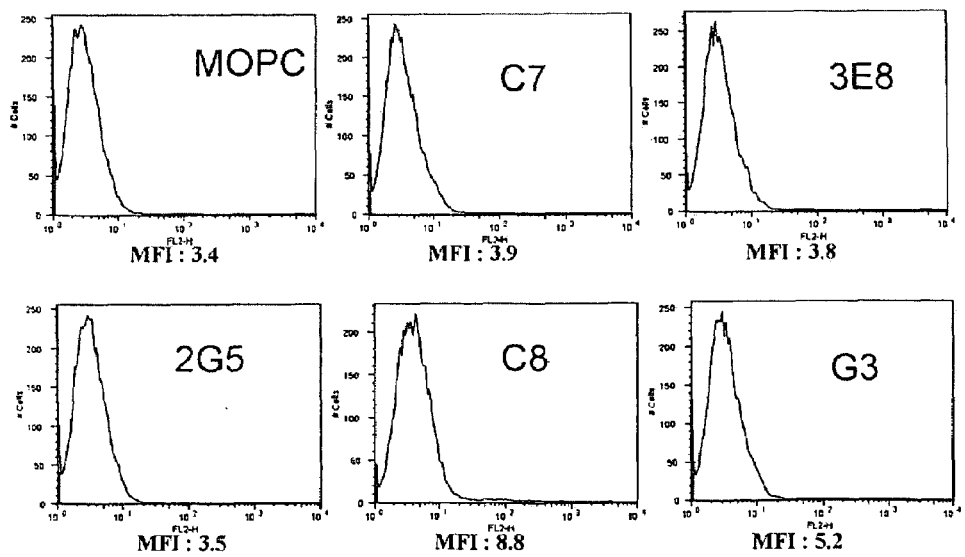

Figure 3. FACS analysis demonstrates that PRLR mAbs are specific to human PRLR.
C. MX-1 cells
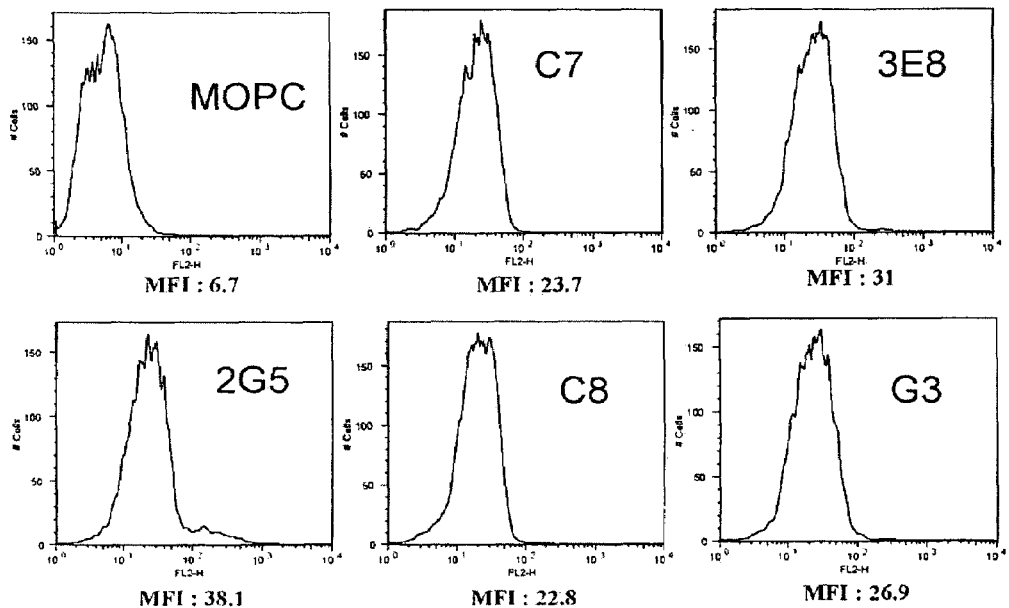
D. HC-11 cells
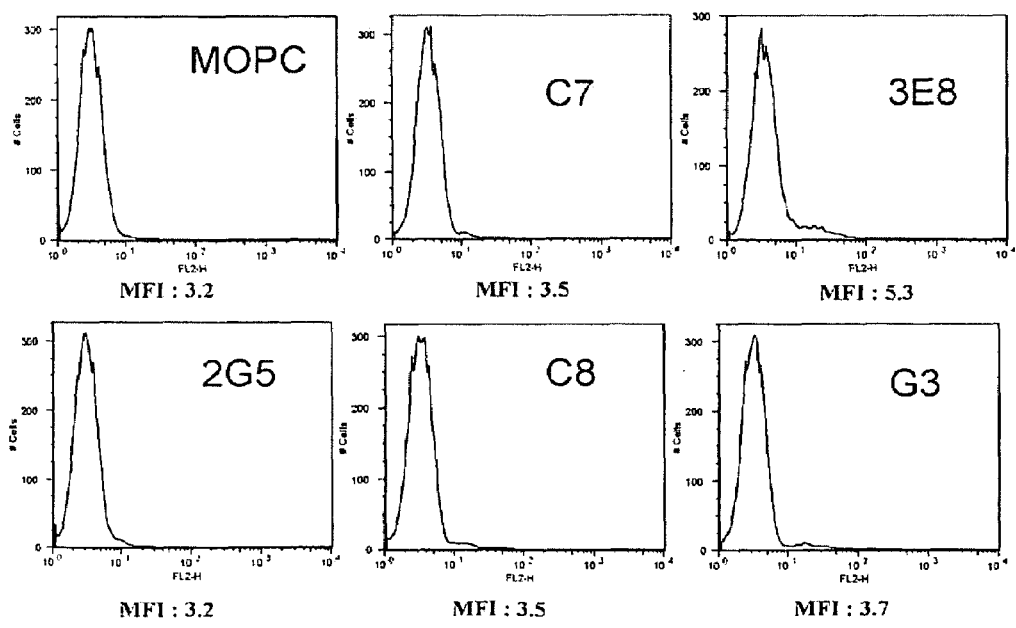

Figure 4. Inhibition of PRL-mediated signaling by PRLR mAbs
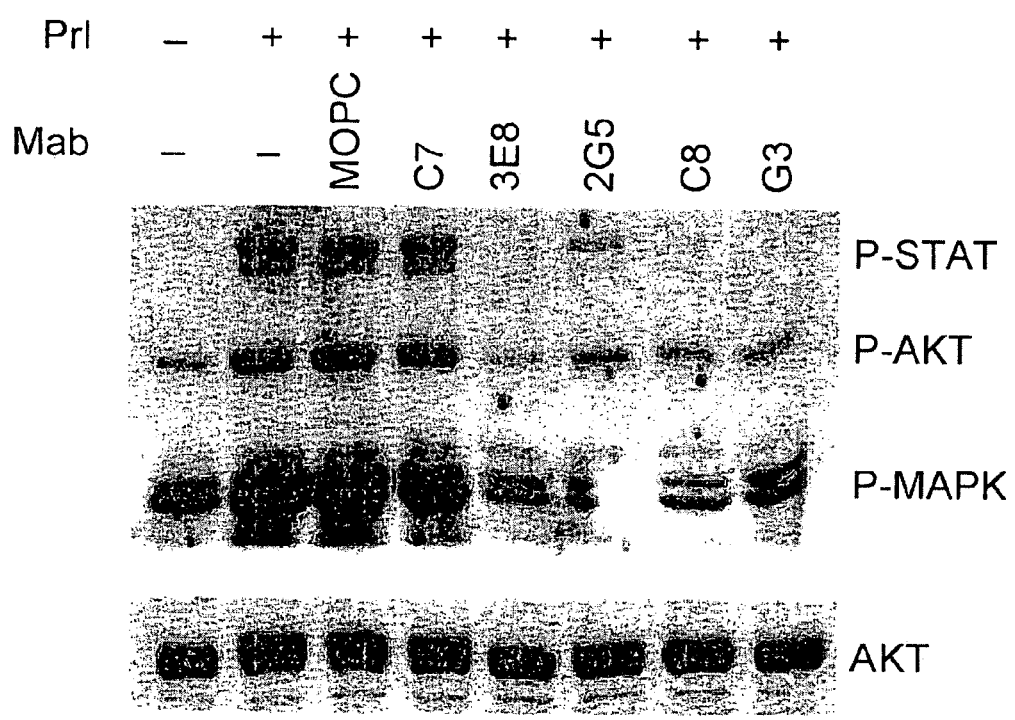

Figure 5. Inhibition of Prl-mediated cell proliferation by PRLR antibodies
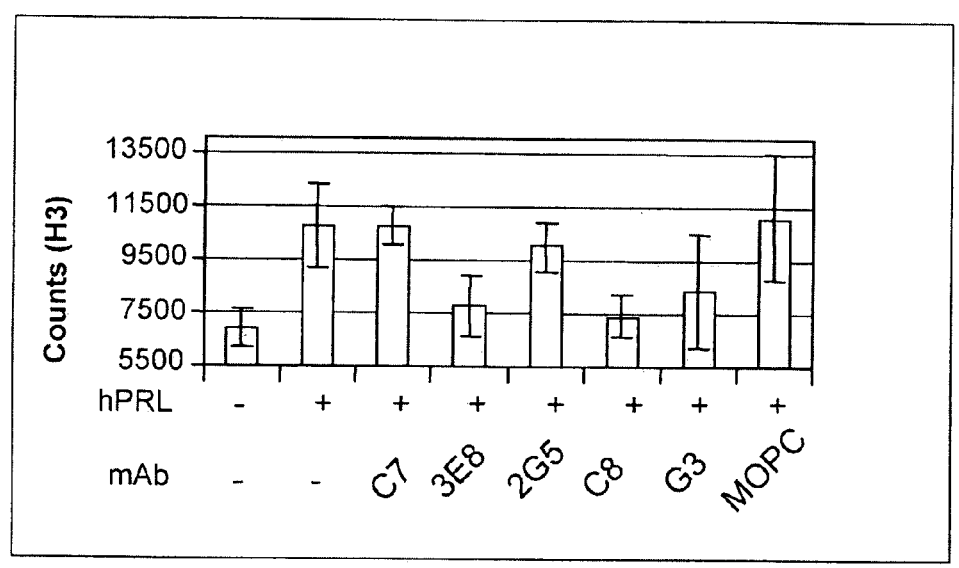

ANTIBODIES TO THE HUMAN PROLACTIN RECEPTOR

CROSS REFERENCE TO RELATED APPLICATIONS

This application claims priority from U.S. Provisional Patent Application No. 60/724,054, filed Oct. 5, 2005. The prior application is incorporated herein by reference in its entirety.

TECHNICAL FIELD

This invention relates to antibodies, particularly antibodies to the human prolactin receptor and uses thereof.

BACKGROUND

Prolactin (PRL) is a neuroendocrine pituitary hormone that is essential for lactogenesis in mammals. The prolactin receptor (PRLR) is a type I transmembrane protein that belongs to the cytokine hematopoeitic receptor superfamily. Both PRL and PRLR play essential roles in breast development and lactation during pregnancy. PRL is produced primarily in the pituitary gland during pregnancy, and interacts with PRLR molecules on mammary epithelial cells in the breast to cause cell proliferation and differentiation during pregnancy. In addition to its primary role in breast development and lactation during pregnancy, it has been postulated that this hormone/receptor pair has additional physiological roles, including regulation of certain aspects of the immune system. Indeed, PRL has been found to be expressed from extrapituitary sources such as the placenta, the normal breast and certain immune cells.

PRL and PRLR have a long-suspected role in breast cancer for several reasons. First, PRL over-expression in mouse models causes mammary tumorigenesis. Second, administration of human PRL to several human breast cancer cells in vitro stimulates their proliferation. Third, a large epidemiological study has shown that there is a positive correlation in women between their circulating serum PRL levels and risk for developing breast cancer (Hankinson et al., J. Natl. Cancer Inst. 91(7):629-34 (1999)). Lastly, several reports indicate that both PRL and PRLR are over-expressed in a high percentage of breast cancer specimens.

At the molecular level, PRL exerts its effects on cells by binding to the PRLR, leading to receptor dimerization and intracellular signaling. PRLR dimerization leads to activation of the receptor via phosphorylation of certain tyrosine residues in the cytoplasmic tail of the receptor. This in turn leads to signaling and activation of the JAK/STAT and Ras pathways. Hyperactivation of Ras signaling is a common feature in a wide variety of human cancers and is known to stimulate cell proliferation and cell survival. Thus, there is strong molecular evidence for a role of PRL signaling in breast cancer, and inhibition of this signaling to MAPK and AKT would be expected to have therapeutic benefit.

The discovery that PRLR and PRL expression is upregulated in a high percentage of breast cancers and/or certain breast cancer cell lines has led to the proposal that inhibition of PRL signaling through its receptor in breast cancers could be therapeutically useful to breast cancer patients. Accordingly, several therapeutic strategies have been developed to inhibit PRL signaling, such as the development of PRL antagonists. One such antagonist is the mutant PRL G129R, which has been shown to inhibit PRL signaling and cause apoptosis in human breast cancer cell lines in vitro. G129R also inhibits breast tumor growth in mouse xenograft models in vivo (Chen et al., Int. J. Oncol. 20:813-818 (2002); Chen et al., Clin. Cancer Res. 5:3583-3593 (1999)). Therefore, the PRL-PRLR signaling pathway is a potential target for breast cancer therapy development.

SUMMARY

The present invention provides antibodies that bind specifically to the prolactin receptor (PRLR) with high affinities. Preferred antibodies have the desired properties of being able to inhibit prolactin (PRL) binding to PRLR, PRL-mediated signaling to the JAK/STAT and RAS pathways, and PRL-mediated cell proliferation. These antibodies are thus useful as therapeutics for cancers that express PRLR, especially breast cancers.

Accordingly, one aspect of the present invention provides an isolated antibody that recognizes a human prolactin receptor and preferably does not bind the mouse prolactin receptor, wherein the antibody inhibits signaling through the human prolactin receptor. Preferably, the antibody inhibits prolactin-induced proliferation of a cell, such as a breast cancer cell. The antibody binds to the human prolactin receptor with an affinity that is preferably 10 nM or less, more preferably 3 nM or less, even more preferably 1 nM or less, and most preferably 0.3 nM or less.

In specific embodiments, the present invention provides a hybridoma deposited at the American Type Culture Collection (ATCC) as PTA-6477, PTA-6478, PTA-6479, PTA-6480, or PTA-6481, as well as an antibody that is produced directly from any of these hybridomas. Also provided are antibodies that recognize the same epitope as an antibody directly produced by any of these hybridomas. Such antibodies include, without being limited to, humanized antibodies, chimeric antibodies, single chain antibodies, Fab fragments, Fab' fragments, F(ab')2 fragments, and Fv fragments. The antibody of the present invention may also be an immunoconjugate, such as an antibody comprising a detectable label.

Another aspect of the present invention provides a pharmaceutical composition comprising the antibody of the present invention. The pharmaceutical composition may further comprise an additional antibody and/or a chemotherapeutic agent. The additional antibody may or may not recognize the prolactin receptor. For example, the additional antibody may be Herceptin®.

Yet another aspect of the present invention provides a nucleic acid that comprises a sequence encoding the antibody of the present invention, pharmaceutical compositions comprising the nucleic acid, vectors comprising the nucleic acid, and host cells comprising the vector. The vector may be any plasmid, including expression vectors. The host cell may be any suitable host cell, such as bacterial, yeast, insect, and mammalian cells. Also provided is a method of producing an antibody comprising culturing the host cell and harvesting the antibody from the culture of the host cell. For example, the antibody may be harvested from the culture supernatant.

Another aspect of the present invention provides a kit comprising at least one antibody of the present invention. The kit may also comprise an additional antibody, a means for detecting the antibody of the invention, a means for administering the antibody, and/or package instructions.

A further aspect of the present invention provides a method of inhibiting signaling through a prolactin receptor in a cell, comprising contacting the cell with an effective amount of the antibody of the present invention. The cell is preferably a breast cancer cell. Alternatively, the cell may be a colon cancer cell, prostate cancer cell, uterine cancer cell, leukemia cell or kidney cancer cell. Preferably, the cell is a cancer cell over-expressing the prolactin receptor.

Another aspect of the present invention provides a method of inhibiting prolactin-induced proliferation of a cell, comprising contacting the cell with the antibody of the present invention. Such inhibition may be measured by any method known in the art and is preferably at least about 20%, more preferably at least about 40%, even more preferably at least about 60%, and most preferably at least about 80%. The cell is preferably a breast cancer cell. Alternatively, the cell may be a colon cancer cell, prostate cancer cell, uterine cancer cell, leukemia cell or kidney cancer cell. Preferably, the cell is a cancer cell over-expressing the prolactin receptor.

Also provided is a method of treating breast cancer in a mammal, comprising administering an effective amount of the antibody of the present invention to the mammal. Optionally, an effective amount of an additional antibody or a chemotherapeutic agent may also be administered to the mammal. The additional antibody may or may not recognize the prolactin receptor. For example, the additional antibody may be Herceptin®. The mammal is preferably a human.

Similarly provided are methods of treating a cancer that expresses PRLR, comprising administering an effective amount of the antibody of the present invention to the mammal. The methods are useful for the treatment of, for example, colon cancer, prostate cancer, uterine cancer, leukemia and kidney cancer. The cancer preferably over-expresses PRLR.

Another aspect of the present invention provides a method for diagnosing or staging a PRLR-expressing cancer using an antibody of the present invention. The cancer preferably over-expresses PRLR. Examples of the cancer include breast cancer, colon cancer, prostate cancer, uterine cancer, leukemia and kidney cancer.

Yet another aspect provides a method of removing a PRLR-expressing cell from a population of mixed cells. The population of mixed cells may be hematopoietic stem cells suitable for transplantation.

DESCRIPTION OF DRAWINGS

FIG. 1: Amino acid sequence of the PRLR-Fc fusion protein (SEQ ID NO:1) used to immunize mice and screen for antibodies.

The amino acid sequence in this figure indicates amino acids 1-448 of the PRLR-Fc fusion protein used to immunize mice and for subsequent screening of hybridoma clones by ELISA. The amino terminal (N-terminal) amino acids 1-214 (bold) constitute the PRLR extracellular domain of the expected mature sequence after cleavage of the signal sequence. The initial amino acid Q represents amino acid 25 of the uncleaved PRLR protein. PRLR amino acids 1-214 are followed by 7 amino acids (underlined) that encode the TEV protease (Tobacco Etch Virus) cleavage site. This site is followed by 227 amino acids (italics) encoding the human IgG$_1$ Fc domain.

FIG. 2: FACS analysis showing that PRLR mAbs recognize PRLR on human breast cancer cell lines. A. FACS analysis of the 5 PRLR mAbs on PRLR-positive T-47D human breast cancer cells shows that the 5 antibodies are able to bind to T-47D cells, while the control MOPC-21 mouse IgG$_1$ control antibody does not. B. A similar FACS analysis on the PRLR-positive MCF-7 human breast cancer cells shows that the PRLR antibodies, but not the control MOPC-21 antibody, recognize PRLR on the surface of these cells. MFI indicates mean fluorescence intensity of the secondary goat anti-mouse PE antibody bound to the indicated primary antibodies. FL2-H indicates fluorescence channel 2, which measures fluorescence from the PE conjugated secondary antibody.

FIG. 3: FACS analysis demonstrates that PRLR mAbs are specific for human PRLR.

The five PRLR mAbs were tested for their ability to recognize human and mouse PRLR by determining their binding activities to 4 different cell populations: A. 293T human kidney cells transiently transfected with a human PRLR expression construct; B. 293T cells transiently transfected with a mouse PRLR expression construct; C. PRLR-positive MX-1 human breast cancer cells, and D. PRLR-positive HC-11 mouse mammary epithelial cells. MFI: mean fluorescence intensity.

FIG. 4: Signaling Assay for Inhibition for PRL Signaling.

T-47D human breast cancer cells, treated by prolactin (Prl) where indicated, were lysed and 40 ug total lysate was loaded onto a 10% SDS-PAGE gel for immunoblot analysis. The blot was probed with mAbs to phospho-STAT5A/B (P-STAT), phospho-p44/42 MAPK (P-MAPK), phospho-AKT (P-AKT), and total AKT (AKT, as a loading control).

FIG. 5: Inhibition of PRL-mediated signaling by PRLR mAbs. Results of a $^3$H-thymidine cell proliferation assay using T-47D human breast cancer cells are shown.

DETAILED DESCRIPTION

The present invention provides antibodies that bind specifically to PRLR with high affinities, and uses thereof. Preferred antibodies have the desired properties of being able to inhibit PRL binding to PRLR, PRL-mediated signaling to the JAK/STAT and RAS pathways, and PRL-mediated cell proliferation. These antibodies are thus useful as therapeutics for cancers that express PRLR, especially breast cancers.

Prior to describing the invention in further detail, the terms used in this application are defined as follows unless otherwise indicated.

I. Definitions

Antibody or Immunoglobulin. In one embodiment, the term "antibody" or "immunoglobulin" molecules encompasses immunospecific fragments thereof, e.g., naturally occurring antibody or immunoglobulin molecules or engineered antibody molecules or fragments that bind antigen in a manner similar to antibody molecules. The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). The term "antibody" (Ab) as used herein includes monoclonal antibodies, polyclonal antibodies, chimeric antibodies, humanized antibodies, human antibodies, multispecific antibodies (e.g., bispecific antibodies), fusion antibodies, immunoconjugates, and antibody fragments, so long as they exhibit the desired specificity.

As will be discussed in more detail below, the term "immunoglobulin" comprises five broad classes of polypeptides that can be distinguished biochemically. All five classes are clearly within the scope of the present invention, and the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H1$, $C_H2$ or $C_H3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H3$ and $C_L$ domains actually comprise the carboxy-terminus of the heavy and light chain, respectively.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1 -γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc., are well characterized and are known to confer functional specialization. Modified versions of each of these classes and isotypes are readily discernable to the skilled artisan in view of the instant disclosure and, accordingly, are within the scope of the instant invention.

As indicated above, the variable region allows the antibody to selectively recognize and specifically bind epitopes on antigens. That is, the $V_L$ domain and $V_H$ domain of an antibody combine to form the variable region that defines a three dimensional antigen binding site. This quaternary antibody structure forms the antigen binding site present at the end of each arm of the Y. More specifically, the antigen binding site is defined by three complementarity determining regions (CDRs) on each of the $V_H$ and $V_L$ chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196: 901-917 (1987), which are incorporated herein by reference in their entireties).

In one embodiment, an antibody of the invention comprises at least one heavy or light chain CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules. Exemplary antibody molecules comprising at least one CDR are known in the art, and exemplary molecules that can be included in the subject antibodies are described herein.

Antibodies or immunospecific fragments thereof for use in the methods of the invention include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to the antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass of immunoglobulin molecule.

Antibody fragments, including single-chain antibodies, may comprise the variable region(s) alone or in combination with the entirety or a portion of the following: hinge region, $C_H1$, $C_H2$, and $C_H3$ domains. Also included in the invention are antigen-binding fragments that also comprise any combination of variable region(s) with a hinge region, $C_H1$, $C_H2$, and $C_H3$ domains. Antibodies or immunospecific fragments thereof for use in the diagnostic and therapeutic methods disclosed herein may be from any animal origin is including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin, and antibodies isolated from human immunoglobulin libraries or from animals transgenic for one or more human immunoglobulins and that do not express endogenous immunoglobulins, as described infra and, for example in, U.S. Pat. No. 5,939, 598 by Kucherlapati et al.

As used herein, the term "heavy chain portion" includes amino acid sequences derived from an immunoglobulin heavy chain. A polypeptide comprising a heavy chain portion comprises at least one of: a $C_H1$ domain, a hinge (e.g., upper, middle, and/or lower hinge region) domain, a $C_H2$ domain, a $C_H3$ domain, or a variant or fragment thereof. For example, an antibody for use in the invention may comprise a polypeptide chain comprising a $C_H1$ domain; a polypeptide chain comprising a $C_H1$ domain, at least a portion of a hinge domain, and a $C_H2$ domain; a polypeptide chain comprising a $C_H1$ domain and a $C_H3$ domain; a polypeptide chain comprising a $C_H1$ domain, at least a portion of a hinge domain, and a $C_H3$ domain, or a polypeptide chain comprising a $C_H1$ domain, at least a portion of a hinge domain, a $C_H2$ domain, and a $C_H3$ domain. In another embodiment, a polypeptide of the invention comprises a polypeptide chain comprising a $C_H3$ domain. Further, an antibody for use in the invention may lack at least a portion of a $C_H2$ domain (e.g., all or part of a $C_H2$ domain). As set forth above, it will be understood by one of ordinary skill in the art that these domains (e.g., the heavy chain portions) may be modified such that they vary in amino acid sequence from the naturally occurring immunoglobulin molecule.

In the antibodies or immunospecific fragments thereof for use in the diagnostic and treatment methods disclosed herein, the heavy chain portions of one polypeptide chain of a multimer may be identical to those on a second polypeptide chain of the multimer. Alternatively, heavy chain portion-containing monomers for use in the methods of the invention are not identical. For example, each monomer may comprise a different target binding site, forming, for example, a bispecific antibody.

The heavy chain portions of an antibody for use in the diagnostic and treatment methods disclosed herein may be derived from different immunoglobulin molecules. For example, a heavy chain portion of a polypeptide may comprise a $C_H1$ domain derived from an $IgG_1$ molecule and a hinge region derived from an $IgG_3$ molecule. In another example, a heavy chain portion can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain portion" includes amino acid sequences derived from an immunoglobulin light chain. Preferably, the light chain portion comprises at least one of a $V_L$ or $C_L$ domain.

An isolated nucleic acid molecule encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a non-essential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence, such as by saturation mutagenesis, and the resultant mutants can be incorporated into antibodies for use in the diagnostic and treatment methods disclosed herein and screened for their ability to bind to the desired antigen, e.g., PRLR.

Antibodies or fragment thereof for use in the diagnostic and therapeutic methods disclosed herein may be described or specified in terms of the epitope(s) or portion(s) of a target polypeptide that they recognize or specifically bind. The portion of an antigen which specifically interacts with the antigen binding domain of an antibody is an "epitope," or an "antigenic determinant." An antigen may comprise a single epitope, but typically, an antigen comprises at least two epitopes, and can include any number of epitopes, depending on the size, conformation, and type of antigen. Antigens are typically peptides or polypeptides, but can be any molecule or compound or a combination of molecules or compounds. For example, an organic compound, e.g., dinitrophenol or DNP, a nucleic acid, a carbohydrate, or a mixture of any of these compounds either with or without a peptide or polypeptide can be a suitable antigen. Thus, for example, an "epitope" on a polypeptide may include a carbohydrate side chain.

The minimum size of a peptide or polypeptide epitope is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide antigens preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred peptides or polypeptides comprising, or alternatively consisting of, antigenic epitopes are at least 10, 15, 20, 25, 30, 35, 40, 45, 50, 55, 60, 65, 70, 75, 80, 85, 90, 95, or 100 amino acid residues in length.

By "specifically binds," it is generally meant that an antibody binds to an epitope via its CDR, and that the binding entails some complementarity between the CDR and the epitope. According to this definition, an antibody is said to "specifically bind" to an epitope when it binds to that epitope, via its CDR more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant (KD) that is less than the antibody's KD for the second epitope. In another non-limiting example, an antibody may be considered to bind a first antigen preferentially if it binds the first epitope with an affinity that is at least one order of magnitude less than the antibody's KD for the second epitope. In another non-limiting example, an antibody may be considered to bind a first epitope preferentially if it binds the first epitope with an affinity that is at least two orders of magnitude less than the antibody's KD for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody for use in the diagnostic and treatment methods disclosed herein may be said to bind a target polypeptide disclosed herein or a fragment or variant thereof with an off rate (k(off)) of less than or equal to $5\times10^{-2}$ sec$^{-1}$, $10^{-2}$ sec$^{-1}$, $5\times10^{-3}$ sec$^{-1}$. More preferably, an antibody of the invention may be said to bind a target polypeptide disclosed herein or a fragment or variant thereof with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

An antibody or fragment thereof for use in the diagnostic and treatment methods disclosed herein may be said to bind a target polypeptide disclosed herein or a fragment or variant thereof with an on rate (k(on)) of greater than or equal to $10^3$ M$^{-1}$ sec$^{-1}$, $5\times10^3$ M$^{-1}$ sec$^{-1}$, 10-4 M$^{-1}$ sec$^{-1}$ or $5\times10^4$ M$^{-1}$ sec$^-$. More preferably, an antibody of the invention may be said to bind a target polypeptide disclosed herein or a fragment or variant thereof with an on rate (k(on)) greater than or equal to $10^5$ M$^{-1}$ sec$^{-1}$, $5\times10^5$ M$^{-1}$ sec-$^{-1}$, $10^6$ M$^{-1}$ sec$^{-1}$, or $5\times10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Antibodies or immunospecific fragments thereof for use in the diagnostic and therapeutic methods disclosed herein may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Antibodies or immunospecific fragments thereof for use in the diagnostic and treatment methods disclosed herein may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Antibodies or immunospecific fragments thereof for use in the diagnostic and treatment methods disclosed herein may act as agonists or antagonists of target polypeptides described herein. For example, an antibody for use in the methods of the present invention may function as an antagonist, blocking or inhibiting PRLR activity.

"Sequence identity" is defined as the percentage of residues in an amino acid or nucleic acid sequence that are identical after aligning the sequence with a reference sequence and introducing gaps, if necessary, to achieve maximal sequence identity. Methods and computer programs for the alignment, such as BLAST, are well known in the art.

As used herein, the term "binding site" or "binding domain" refers to a region of a binding molecule, e.g., a binding polypeptide (e.g., an antibody or fragment thereof), which is responsible for specifically binding to a target molecule of interest (e.g., an antigen, ligand, receptor, substrate or inhibitor). Exemplary binding domains include antibody variable domains, a receptor binding domain of a ligand, or a ligand binding domain of a receptor or an enzymatic domain. A binding domain on an antibody is referred to herein as an "antigen binding domain."

An antibody or immunogenic fragment for use in the diagnostic and treatment methods disclosed herein may be "multispecific," e.g., bispecific, trispecific or of greater multispecificity, meaning that it recognizes and binds to two or more different epitopes present on one or more different antigens (e.g., proteins) at the same time. Thus, whether a binding molecule is "monospecfic" or "multispecific," e.g., "bispecific," refers to the number of different epitopes with which the binding molecule reacts. Multispecific antibodies may be specific for different epitopes of a target polypeptide described herein, or may be specific for a target polypeptide as well as for a heterologous epitope, such as a heterologous polypeptide or solid support material.

As used herein the term "valency" refers to the number of potential binding domains, e.g., antigen binding domains, present in a binding molecule. Each binding domain specifically binds one epitope. When a binding molecule comprises more than one binding domain, each binding domain may specifically bind the same epitope (for an antibody with two binding domains, termed "bivalent monospecific") or to different epitopes (for an antibody with two binding domains, termed "bivalent bispecific"). An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Application Publication Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "$C_H1$ domain" includes the first (most amino terminal) constant region domain of an immunoglobulin heavy chain. The $C_H1$ domain is adjacent to the $V_H$ domain and is amino terminal to the hinge region of an immunoglobulin heavy chain molecule.

As used herein the term "$C_H2$ domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit.). The $C_H2$ domain is unique in that it is not closely paired with another domain. Rather, two N-linked branched carbohydrate chains are interposed between the two $C_H2$ domains of an intact native IgG molecule. It is also well documented that the $C_H3$ domain extends from the $C_H2$ domain to the C-terminal of the IgG molecule and comprises approximately 108 residues.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the $C_H1$ and $C_L$ regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g., mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a fimctional engineered or humanized antibody.

Alterations to the variable region notwithstanding, those skilled in the art will appreciate that, in preferred embodiments, the anti-PRLR antibodies of the instant invention may comprise antibodies, or immunoreactive fragments thereof, in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In selected embodiments, the constant region of these type of anti-PRLR antibodies will comprise a human constant region. Modifications to the constant region compatible with the instant invention comprise additions, deletions or substitutions of one or more amino acids in one or more domains. That is, the anti-PRLR antibodies disclosed herein may comprise alterations or modifications to one or more of the three heavy chain constant domains ($C_H1$, $C_H2$ or $C_H3$) and/or to the light chain constant domain ($C_L$). In especially preferred embodiments the modified antibodies will comprise domain deleted constructs or variants wherein the entire $C_H2$ domain has been removed ($\Delta C_H2$ constructs).

As used herein the term "properly folded polypeptide" includes polypeptides (e.g., antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g., by recombinant techniques, in vitro peptide synthesis, by enzymatic or chemical coupling of peptides or some combination of these techniques).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), may be performed.

An "antibody that inhibits the growth of tumor cells expressing PRLR" or a "growth inhibitory antibody" is one which binds to and results in measurable growth inhibition of cancer cells expressing or over-expressing PRLR. Preferred growth inhibitory anti-PRLR antibodies inhibit growth of PRLR-expressing tumor cells (e.g., breast cancer cells) by at least 20%, more preferably at least about 40%, even more preferably by at least about 60%, and most preferably by at least about 80%, as compared to control cells not treated with the antibody.

An antibody which "induces apoptosis" is one which induces programmed cell death as determined by methods known in the art, such as binding of annexin V, fragmentation of DNA, cell shrinkage, dilation of endoplasmic reticulum, cell fragmentation, and/or formation of membrane vesicles (called apoptotic bodies). Preferably, the antibody which induces apoptosis is one which results in about 2 to 50 fold, preferably about 5 to 50 fold, and most preferably about 10 to 50 fold, induction of annexin binding relative to untreated cell in an annexin binding assay.

A "PRLR-expressing cell" is a cell which expresses endogenous or transfected PRLR on the cell surface. A "PRLR-expressing cancer" is a cancer comprising cells that express endogenous PRLR on the cell surface. A cancer which "over-expresses" PRLR is one which has significantly higher levels of PRLR at the cell surface compared to a noncancerous cell of the same tissue type. Such over-expression may be caused by gene amplification or by increased transcription or translation. PRLR over-expression may be determined in a diagnostic or prognostic assay by evaluating levels of the PRLR protein present on the surface of a cell (e.g., via an immunohistochemistry assay; FACS analysis). Alternatively, or additionally, one may measure levels of PRLR-encoding nucleic acid or MRNA in the cell, e.g., via fluorescent in situ hybridization (FISH), Southern blotting, Northern blotting, or polymerase chain reaction (PCR) techniques, such as real time quantitative PCR (RT-PCR). One may also study PRLR over-expression by measuring shed antigen in a biological fluid such as serum, e.g., using antibody-based assays. Aside from the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

A "mammal" refers to any mammal, including humans, domestic and farm animals, and zoo, sports, or pet animals, such as dogs, cats, cattle, horses, sheep, pigs, goats, rabbits, etc. Preferably, the mammal is human.

By "hyperproliferative disease or disorder" is meant all neoplastic cell growth and proliferation, whether malignant or benign, including all transformed cells and tissues and all cancerous cells and tissues. Hyperproliferative diseases or disorders include, but are not limited to, precancerous lesions, abnormal cell growths, benign tumors, malignant tumors, and "cancer."

Additional examples of hyperproliferative diseases, disorders, and/or conditions include, but are not limited to neoplasms, whether benign or malignant, located in the: prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital tract.

As used herein, the terms "tumor" or "tumor tissue" refer to an abnormal mass of tissue that results from excessive cell division. A tumor or tumor tissue comprises "tumor cells" which are neoplastic cells with abnormal growth properties and no useful bodily function. Tumors, tumor tissue and tumor cells may be benign or malignant. A tumor or tumor tissue may also comprise "tumor-associated non-tumor cells", e.g., vascular cells which form blood vessels to supply the tumor or tumor tissue. Non-tumor cells may be induced to replicate and develop by tumor cells, for example, the induction of angiogenesis in a tumor or tumor tissue.

As used herein, the term "malignancy" refers to a non-benign tumor or a cancer. As used herein, the term "cancer" connotes a type of hyperproliferative disease which includes a malignancy characterized by deregulated or uncontrolled cell growth. Examples of cancer include, but are not limited to, carcinoma, lymphoma, blastoma, sarcoma, and leukemia or lymphoid malignancies. More particular examples of such cancers are noted below and include: squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The method of the present invention may be used to treat premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W.B. Saunders Co., Philadelphia, pp. 68-79 (1976).

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

Hyperplasia is a form of controlled cell proliferation, involving an increase in cell number in a tissue or organ, without significant alteration in structure or function. Hyperplastic disorders which can be treated by the method of the invention include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, focal epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia.

Metaplasia is a form of controlled cell growth in which one type of adult or fully differentiated cell substitutes for another type of adult cell. Metaplastic disorders which can be treated by the method of the invention include, but are not limited to, agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, and symptomatic myeloid metaplasia.

Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation. Dysplastic disorders which can be treated by the method of the invention include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia ofjaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, ophthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated by the method of the invention include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

As used herein, the terms "treat" or "treatment" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

For example, a subject is successfully "treated" for a PRLR-expressing cancer if, after receiving a therapeutic amount of an anti-PRLR antibody according to the methods of the present invention, the patient shows one or more of the following at an observable and/or measurable level: reduction in the number of cancer cells; reduction in the tumor size; inhibition or elimination of cancer cell infiltration into peripheral organs, including the spread of cancer into soft tissue and bone; inhibition or elimination of tumor metastasis; inhibition of tumor growth; reduction of one or more of the symptoms associated with the specific cancer; and reduced morbidity and mortality.

The above parameters for assessing successful treatment and improvement in the disease can be determined by routine procedures familiar to a physician. For cancer therapy, efficacy can be measured, for example, by assessing the time to disease progression and/or determining the response rate. Metastasis can be determined by staging tests, bone scan, and tests for calcium level and other enzymes to determine spread to the bone. Chest X-rays and measurement of liver enzyme levels by known methods are used to look for metastasis to the lungs and liver, respectively.

An "effective amount" is an amount sufficient for an intended use. The term "therapeutically effective amount" refers to an amount of an antibody or a drug effective to treat a disease or disorder in a subject.

"Carriers" as used herein include pharmaceutically acceptable carriers, excipients, or stabilizers which are nontoxic to a cell or mammal at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; peptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, Y90, $Re^{186}$, $Re^{188}$, $Sm^{153}$, $Bi^{212}$, $P^{32}$ and radioactive isotopes of Lu), chemotherapeutic agents, enzymes and fragments thereof such as nucleolytic enzymes, antibiotics, and toxins such as small molecule toxins or enzymatically active toxins of bacterial, fungal, plant or animal origin, including fragments and/or variants thereof.

A "detectable label" as used herein refers to a detectable compound or composition which is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition which is detectable.

A "small molecule" is defined herein to have a molecular weight below about 500 Daltons.

The term "package instructions" is used to refer to instructions customarily included in commercial packages of therapeutic products, that contain information about the indications, usage, dosage, administration, contraindications and/or warnings concerning the use of such therapeutic products.

An "isolated nucleic acid" is a nucleic acid, e.g., an RNA, DNA, or a mixed polymer, which is substantially separated from other genome DNA, proteins, or complexes such as ribosomes and polymerases, which naturally accompany a native sequence. The term embraces a nucleic acid sequence which has been removed from its naturally occurring environment, and includes recombinant or cloned DNA isolates, chemically synthesized nucleic acids, and nucleic acids biologically synthesized by heterologous systems.

II. Compositions

To prepare anti-PRLR antibodies, a fusion protein comprising the extracellular domain of the human PRLR and the Fc domain of immunoglobulin was used to generate monoclonal antibodies (Example 1). The antibodies were screened for their binding activities, and five hybridomas were further analyzed. These five hybridomas are designated 4P1E9.C7, 4P1B3.3E8, 4P1E5.2G5, 4P4F1.C8, and 4P4H6.G3, also referred to in this application as C7, 3E8, 2G5, C8 and G3, respectively.

These hybridomas produce monoclonal antibodies that have high affinities for the human PRLR, at the $10^{-8}$ M, $10^{-9}$ M, and $10^{-10}$ M levels (Example 1). The antibodies are specific for human PRLR and do not bind the mouse PRLR (Example 2). However, the antibodies do not compete with one another for binding to the human PRLR. Therefore, they each recognize a different epitope in the human PRLR (Example 1).

With the exception of C7, the antibodies blocked PRL binding to PRLR (Example 3). Furthermore, the antibodies that blocked PRL-PRLR binding also inhibited phosphorylation of MAPK, AKT and STAT that is induced by PRL (Example 4). Therefore, the antibodies produced by 3E8, 2G5, C8 and G3 can be used to inhibit PRL-PRLR signaling. The antibodies from 3E8, C8 and G3 also effectively inhibited T-47D breast cancer cell proliferation (Example 5). Although the 2G5 antibody was not effective against T-47D cell proliferation in the studies described herein, it is contemplated that it may be used to inhibit cell growth of other cancer cells, particularly cells with a higher PRLR level than T-47D cells.

The hybridomas were deposited at the American Type Culture Collection (ATCC) under the Budapest Treaty on Dec. 21, 2004. The ATCC designations for the hybridomas are as follows:

TABLE 1

| ATCC designations of the hybridomas | | |
| --- | --- | --- |
| Hybridoma | Abbreviated as | ATCC designation |
| 4P1E9.C7 | C7 | PTA-6477 |
| 4P1B3.3E8 | 3E8 | PTA-6478 |
| 4P1E5.2G5 | 2G5 | PTA-6479 |
| 4P4F1.C8 | C8 | PTA-6480 |
| 4P4H6.G3 | G3 | PTA-6481 |

Accordingly, the present invention provides isolated antibodies that recognize the human PRLR and preferably do not recognize the mouse PRLR. The antibodies bind to the human PRLR with an affinity of less than 10 nM, more preferably less than 3 nM, even more preferably less than 1 nM, and most preferably less than 0.3 nM. Particularly provided are antibodies capable of blocking the binding between PRL and the human PRLR receptor, inhibiting PRL signal transduction, and/or inhibiting cancer cell proliferation/survival.

In specific embodiments, the present invention provides a hybridoma deposited at the ATCC as PTA-6477, PTA-6478, PTA-6479, PTA-6480, or PTA-6481. Also provided are isolated antibodies that recognize the same epitope as any one of these hybridomas. The antibody may be directly produced from the hybridomas, or it may be an antibody that recognizes the same epitope because it comprises at least part of the antigen-binding regions of an antibody produced by the hybridomas. These antibodies, and the preparation thereof, are discussed in further detail below.

A. Production of Various Anti-PRLR Antibodies

Exemplary techniques are described for the production of the antibodies useful in the present invention. The PRLR antigen to be used for production of antibodies may be, e.g., the full length polypeptide or a portion thereof. Alternatively, cells expressing PRLR at their cell surface (e.g., CHO or NIH-3T3 cells transformed to over-express PRLR; breast or other PRLR-expressing tumor cell line), or membranes prepared from such cells, can be used to generate antibodies. The nucleotide and amino acid sequences of human and murine PRLR are available in the art. PRLR can be produced recombinantly in and isolated from, bacterial or eukaryotic cells using standard recombinant DNA methodology. PRLR can be expressed as a tagged (e.g., epitope tag) fusion protein or other fusion protein to facilitate isolation and identification in various assays. Antibodies or binding proteins that bind to various tags and fusion sequences are available as elaborated below. Other forms of PRLR useful for generating antibodies will be apparent to those skilled in the art.

1. Tags

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et aL, Protein Engineering, 3(6):547-553 (1990)). The FLAG-peptide (Hopp et al., BioTechnology, 6:1204-1210 (1988)) is recognized by an anti-FLAG M2 monoclonal antibody (Eastman Kodak Co., New Haven, Conn.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Other tag polypeptides include the KT3 epitope peptide (Martin et al., Science, 255:192-194 (1992)); an a-tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)).

2. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R_1N=C=NR$, where R and $R_1$ are different alkyl groups.

Animals are typically immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

3. Monoclonal Antibodies

Monoclonal antibodies may be made using the hybridoma method first described by Kohler et al., Nature, 256:495 (1975), or may be made by recombinant DNA methods (e.g., U.S. Pat. No. 4,816,567).

In the hybridoma method, a mouse or other appropriate host animal, such as a hamster, is immunized as described above to elicit lymphocytes that produce antibodies specifically binding to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell.

The hybridoma cells thus prepared are seeded and grown in a suitable culture medium which preferably contains one or more substances that inhibit the growth or survival of the unfused, parental myeloma cells (also referred to as fusion partner). Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors, and SP-2 and derivatives, e.g., X63-Ag8-653 cells. Human myeloma and mouse-human heteromyclonia cell lines also have been described for the production of human monoclonal antibodies.

Culture medium in which hybridoma cells are growing is assayed for production of monoclonal antibodies directed against the antigen. For example, the binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis or the methods described herein.

Once hybridoma cells that produce antibodies of the desired specificity, affinity, and/or activity are identified, the clones may be subcloned by limiting dilution procedures and grown by standard methods. In addition, the hybridoma cells may be grown in vivo as ascites tumors in an animal, e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

Monoclonal antibodies or antibody fragments can also be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences, or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

4. Humanized Antibodies

Methods for humanizing non-human antibodies have been described in the art. A humanized antibody has one or more amino acid residues introduced into it from a source which is non-human. Humanization can be essentially performed following the method of Winter and co-workers (Jones et al., Nature, 321:522-525 (1986); Reichmann et al., Nature, 332: 323-327 (1988); Verhoeyen et al., Science, 239:1534-1536 (1988)), by substituting hypervariable region sequences for the corresponding sequences of a human antibody. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol. 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA 89:4285 (1992); Presta et al., J. Immunol. 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-PRLR antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact $IgG_1$ antibody.

5. Human Antibodies

As an alternative to humanization, human antibodies can be generated (e.g., van Dijk et al., Curr Opin Chem Biol. 5(4):368-74 (2001)). For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice can result in the production of human antibodies upon antigen challenge.

Alternatively, phage display technology can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Human antibodies may also be generated by in vitro activated B cells (see, e.g., U.S. Pat. Nos. 5,567,610 and 5,229,275).

A human antibody with a desired specificity, such as one that recognizes the same epitope as the anti-PRLR hybridomas described herein, can be identified by competitive ELISA or other methods known in the art.

6. Antibody Fragments

In certain circumstances there are advantages of using antibody fragments, rather than whole antibodies. For example, the smaller size of the fragments allows for rapid clearance, and may lead to improved access to solid tumors.

Traditionally, antibody fragments were derived via proteolytic digestion of intact antibodies. Alternatively, these fragments can be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. The antibody fragment may also be a "linear antibody", e.g., as described in U.S. Pat. No. 5,641,870. Such linear antibody fragments may be monospecific or bispecific.

7. Bispecific Antibodies

Bispecific antibodies are antibodies that have binding specificities for at least two different epitopes. Exemplary bispecific antibodies may bind to two different epitopes of the PRLR protein. Other such antibodies may combine an PRLR binding site with a binding site for another protein. Alternatively, an anti-PRLR arm may be combined with an arm which binds to a triggering molecule on a leukocyte such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the PRLR-expressing cell. Bispecific antibodies may also be used to localize cytotoxic agents to cells which express PRLR. These antibodies possess a PRLR-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-539 (1983)). In a different approach, antibody variable domains with the desired binding specificities are fused to immunoglobulin constant domain sequences. DNAs encoding the immunoglobulin heavy chain fusions and, if desired, the immunoglobulin light chain, are inserted into separate expression vectors, and are co-transfected into a suitable host cell. This provides for greater flexibility in adjusting the proportions of the three polypeptide fragments. It is, however, possible to insert the coding sequences for two or all three polypeptide chains into a single expression vector when the expression of at least two polypeptide chains in equal ratios results in high yields.

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods.

The "diabody" technology provides an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites.

8. Multivalent Antibodies

A multivalent antibody may be internalized (and/or catabolized) faster than a bivalent antibody by a cell expressing an antigen to which the antibodies bind. The antibodies of the present invention can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or peptide spacer, and n is 0 or 1.

9. Other Amino Acid Sequence Modifications

Amino acid sequence modification(s) of the anti-PRLR antibodies described herein are contemplated. For example, it may be desirable to improve the binding affinity and/or other biological properties of the antibody. Amino acid sequence variants of the anti-PRLR antibody are prepared by introducing appropriate nucleotide changes into the anti-PRLR antibody nucleic acid, or by peptide synthesis. Such modifications include, for example, deletions from, and/or insertions into and/or substitutions of, residues within the amino acid sequences of the anti-PRLR antibody. Any combination of deletion, insertion, and substitution is made to arrive at the final construct, provided that the final construct possesses the desired characteristics. The amino acid changes also may alter post-translational processes of the anti-PRLR antibody, such as changing the number or position of glycosylation sites.

A useful method for identification of certain residues or regions of the anti-PRLR antibody that are preferred locations for mutagenesis is called "alanine scanning mutagenesis". In this method, a residue or group of target residues are identified (e.g., charged residues such as arg, asp, his, lys, and glu) and replaced by a neutral or negatively charged amino acid (most preferably alanine or polyalanine) to affect the interaction of the amino acids with PRLR antigen. Those amino acid locations demonstrating functional sensitivity to the substitutions then are refined by introducing further or other variants at, or for, the sites of substitution. For example, to analyze the performance of a mutation at a given site, ala scanning or random mutagenesis is conducted at the target codon or region and the expressed anti-PRLR antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-PRLR antibody with an N-terminal methionyl residue or the antibody fused to a cytotoxic polypeptide. Other insertional variants of the anti-PRLR antibody molecule include the fusion to the N— or C-terminus of the anti-PRLR antibody of an enzyme (e.g., for ADEPT) or a polypeptide which increases the serum half-life of the antibody.

Another type of variant is an amino acid substitution variant. These variants have at least one amino acid residue in the anti-PRLR antibody molecule replaced by a different residue. The sites of greatest interest for substitutional mutagenesis include the hypervariable regions, but FR alterations are also contemplated.

Any cysteine residue not involved in maintaining the proper conformation of the anti-PRLR antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human PRLR. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in, e.g., U.S. Pat. No. 5,739,277. A salvage receptor binding epitope is an epitope of the Fc region of an IgG molecule (e.g., IgG, $IgG_2$, IgG3, or $IgG_4$) that is responsible for increasing the in vivo serum half-life of the IgG molecule.

10. Screening for Antibodies with the Desired Properties

Techniques for generating antibodies have been described above. One may further select antibodies with certain biological characteristics, as desired.

The growth inhibitory effects of an anti-PRLR antibody of the invention may be assessed by methods known in the art, e.g., using cells which express PRLR either endogenously or following transfection with the PRLR gene. For example, the tumor cell lines and PRLR-transfected cells provided in the Examples may be treated with an anti-PRLR monoclonal antibody of the invention at various concentrations for a few days (e.g., 2-7), and stained with crystal violet or MTT. Another method of measuring proliferation would be by comparing $^3$H-thymidine uptake by the cells treated in the presence or absence an anti-PRLR antibody of the invention. Appropriate positive controls include treatment of a selected cell line with a growth inhibitory antibody known to inhibit growth of that cell line. Growth inhibition of tumor cells in vivo can be determined in various ways, such as using a nude mouse bearing a tumor graft. Preferably, the tumor cell is one that over-expresses PRLR. Preferably, the anti-PRLR antibody inhibits cell proliferation of a PRLR-expressing tumor cell in vitro or in vivo by about 20-100% compared to the untreated tumor cell, more preferably by about 40-100%, and even more preferably by about 60-100% or 80-100%, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-PRLR antibody at about 1 µg/kg to about 100 mg/kg body weight results in reduction in tumor size or tumor cell proliferation within about 5 days to 3 months from the first administration of the antibody, preferably within about 5 to 30 days.

To select for antibodies which induce cell death, loss of membrane integrity may be assessed as indicated by, e.g., propidium iodide (PI), trypan blue or 7AAD uptake. A PI uptake assay can be performed in the absence of complement and immune effector cells. PRLR-expressing tumor cells are incubated with medium alone or medium containing of the appropriate monoclonal antibody at, e.g., about 10 µ/ml. The cells are incubated for a 3 day time period. Following each treatment, cells are washed and clumps removed. The cells then receive PI (10 µg/ml) and are analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

To screen for antibodies which bind to an epitope on PRLR that is bound by an antibody of interest, a routine cross-blocking assay such as that described in Antibodies, A Laboratory Manual, Cold Spring Harbor Laboratory, Ed Harlow and David Lane (1988), can be performed. This assay can be used to determine if a test antibody binds the same site or epitope as an anti-PRLR antibody of the invention. Alternatively, or additionally, epitope mapping can be performed by methods known in the art. For example, the antigen sequence can be mutagenized such as by alanine scanning, to identify contact residues. In a different method, peptides corresponding to different regions of PRLR can be used in competition assays with the test antibodies.

11. Immunoconjugates

The invention also provides immunoconjugates comprising an antibody conjugated to an anti-cancer agent such as a cytotoxic agent or chemotherapeutic agents.

Conjugates of an antibody and one or more small molecule toxins, such as a calicheamicin, maytansinoids, a trichothene, and CC1065, and the derivatives of these toxins that have toxin activity, are also contemplated herein.

Examples of other chemotherapeutic agents that can be conjugated to the anti-PRLR antibodies of the invention include BCNU, streptozoicin, vincristine and 5-fluorouracil, as well as esperamicins.

Enzymatically active toxins and fragments thereof which can be used include diphtheria A chain, nonbinding active fragments of diphtheria toxin, exotoxin A chain (from Pseudomonas aeruginosa), ricin A chain, abrin A chain, modeccin A chain, α-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-PRLR antibodies. Examples include $At^{211}$, $I^{131}$, $I^{125}$, $Y^{90}$, $Re^{186}$, $Rc^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $Tc^{99m}$ or $I^{123}$, or a spin label for nuclear magnetic resonance (NMR) imaging (also known as magnetic resonance imaging, MRI), such as $iodine^{123}$, $iodine^{131}$, $indium^{111}$, $fluorine^{19}$, $carbon^{13}$, $nitrogen^{15}$, $oxygen^{17}$, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, $fluorine^{19}$ in place of hydrogen. Labels such as $Tc^{99m}$ or $I^{123}$, $Re^{186}$, $Re^{188}$ and $In^{111}$ can be attached via a cysteine residue in the peptide. $Y^{90}$ can be attached via a lysine residue. The IODOGEN method (Fraker et al (1978) Biochem. Biophys. Res. Commun. 80:49-57) can be used to incorporate $iodine^{123}$.

Conjugates of the antibody and cytotoxic agent may be made using a variety of bifunctional protein coupling agents such as N-succinimidyl-3-(2-pyridyldithio)propionate (SPDP), succinimidyl-4(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azido-benzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4dinitrobenzene). Carbon-14-labeled 1-isothiocyanatobenzyl-3-methyldiethylene triaminepentaacetic acid (MX-DTPA) is an exemplary chelating agent for conjugation of radionucleotide to the antibody. The linker may be a cleavable linker, facilitating release of the cytotoxic drug in the cell.

Alternatively, a fusion protein comprising the anti-PRLR antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

12. Antibody Dependent Enzyme Mediated Prodrug Therapy (ADEPT)

The antibodies of the present invention may also be used in ADET by conjugating the antibody to a prodrug-activating enzyme which converts a prodrug to an active anti-cancer drug.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs.

The enzymes can be covalently bound to the anti-PRLR antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art.

13. Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions.

The anti-PRLR antibodies disclosed herein may also be formulated as immunoliposomes. The components of the liposome are commonly arranged in a bilayer formation, similar to the lipid arrangement of biological membranes. Liposomes containing the antibody can be prepared by methods known in the art.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired a diameter. Fab' fragments of the antibody of the present invention can be conjugated to the liposomes via a disulfide interchange reaction. A chemotherapeutic agent can be optionally contained within the liposome.

B. Nucleic Acids, Vctors and Host Cells

The invention also provides isolated nucleic acids encoding the anti-PRLR antibodies of the present invention, vectors and host cells comprising the nucleic acids, and methods for producing the antibodies using the nucleic acids.

DNA encoding the monoclonal antibodies of the present invention, in particular the C7, 3E8, 2G5, C8 and G3 antibodies, can be readily isolated and sequenced using conventional procedures (e.g., by using oligonucleotide probes that are capable of binding specifically to genes encoding the heavy and light chains of the antibody). The DNA can then be inserted into a vector for recombinant DNA manipulations (e.g., to make chimeric antibodies) or protein expression. The vector components generally include, but are not limited to, one or more of the following: a signal sequence, an origin of replication, one or more marker genes, an enhancer element, a promoter, and a transcription termination sequence.

Suitable host cells for cloning or expressing the DNA in the vectors herein include prokaryote, yeast, or higher eukaryote cells. Suitable prokaryoles for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis, Pseudomonas* such as *P. aeruginosa*, and *Streptomyces*.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. For expression of antibody fragments and polypeptides in bacteria, see, e.g., U.S. Pat. Nos. 5,648,237, 5,789,199, and 5,840,523. After expression, the antibody is isolated from the *E. coli* cell paste in a soluble fraction and can be purified through, e.g., a protein A or G column depending on the isotype.

In addition to prokaryotes, eukaryotic microbes such as filamentous fungi or yeast are suitable cloning or expression hosts for anti-PRLR antibody-encoding vectors. Saccharomyces cerevisiae, or common baker's yeast, is the most commonly used among lower eukaryotic host microorganisms. However, a number of other genera, species, and strains are commonly available and useful herein, such as Schizosaccharomyces pombe; Kluyveromyces hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia; Pichia pastoris; Candida; Trichoderma reesia; Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-PRLR antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopicius* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells; MRC 5 cells; FS4 cells; and a human hepatoma line (Hep G2).

The antibody composition produced by the host cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma_1$, $\gamma_2$, or $\gamma_4$ heavy chains. Protein G is recommended for all mouse isotypes and for human y3. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

C. Pharmaceutical Compositions

Pharmaceutical compositions comprising the antibodies of the present invention can be prepared by mixing an antibody having the desired degree of purity with optional pharmaceutically acceptable carriers, excipients or stabilizers (see, e.g., Gennaro, Remington: The Science and Practice of Pharmacy, 20th Edition (Baltimore, Md.: Lippincott Williams & Wilkins, 2000)) in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); peptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN™, PLURONICS™, or polyethylene glycol (PEG). The antibody preferably comprises the antibody at a concentration of between 5-200 mg/ml, preferably between 10-100 mg/ml.

The pharmaceutical composition may also contain more than one active compound for the particular indication being treated, preferably those with complementary activities that do not adversely affect each other. For example, in addition to the anti-PRLR antibody, it may be desirable to include an additional antibody, e.g., a second anti-PRLR antibody which binds a different epitope on PRLR, or an antibody to another target such as a growth factor that affects the growth of the particular cancer. For example, Herceptin® can be combined with the anti-PRLR antibody to treat breast cancer, particularly estrogen-dependent breast cancer. Alternatively or additionally, the composition may further comprise a chemotherapeutic agent, cytotoxic agent, cytokine, and/or anti-hormonal agent. Such molecules are suitably present in combination in amounts that are effective for the purpose intended.

The active ingredients may also be entrapped in microcapsules (for example, hydroxymethylcellulose or gelatin-microcapsules and polymethylmethacylate microcapsules), in colloidal drug delivery systems (for example, liposomes, albumin microspheres, microemulsions, nano-particles and nanocapsules), or in macroemulsions.

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxyburyric acid.

The formulations to be used for in vivo administration must be sterile. This is readily accomplished by filtration through sterile filtration membranes.

D. Kits

Kits are also provided that are useful for various purposes, e.g., for diagnosis, therapeutic uses, cell killing assays, or purification or immunoprecipitation of PRLR from cells. In addition to the antibodies of the present invention (or nucleic acids or hybridoma thereof), the other components of the kits depend on the purposes. For instance, for therapeutic uses, the kit may contain additional therapeutic agents to be used in conjunction with the antibodies. For diagnosis, the kits may comprise means to detect antibody binding, such as secondary antibodies and reagents for ELISA or other immunoassays. For isolation and purification of PRLR, the kit can contain an anti-PRLR antibody coupled to beads (e.g., sepharose beads). Kits can be provided which contain the antibodies for detection and quantitation of PRLR in vitro, e.g., in an ELISA or a Western blot. The kit may comprise a container and package instructions on or associated with the container. The container holds a composition comprising at least one anti-PRLR antibody of the invention. Additional containers may be included that contain, e.g., diluents and buffers, or control antibodies. The package instructions may provide a description of the composition as well as instructions for the intended use.

III. Methods

The anti-PRLR antibodies are useful for treating a PRLR-expressing cancer or ameliorating one or more symptoms of the cancer in a mammal. Such a cancer includes breast cancer, colon cancer, prostate cancer, uterine cancer, kidney cancer, leukemia, as well as metastatic cancers of any of the preceding. The cancer preferably over-expresses PRLR. The therapeutic antibody may exert anti-tumor affects by any one of a variety of mechanisms, such as inhibiting cancer cell proliferation, inhibiting cell survival signaling, inducing apoptosis, enabling the cells to be recognized and killed by immune cells or complement, or enhancing their sensitivity to chemotherapy.

The anti-PRLR antibodies of the invention also have various non-therapeutic applications. The anti-PRLR antibodies of the present invention can be useful for diagnosis and staging of PRLR-expressing cancers (e.g., in radioimaging). The antibodies are also useful for purification or immunoprecipitation of PRLR from cells, as well as for detection and quantitation of PRLR in vitro, e.g., in an ELISA or a Western blot. The antibodies can be used to kill and eliminate PRLR-expressing cells from a population of mixed cells as a step in the purification of other cells. In particular, they can be used to purge cancer cells from hematopoietic stem cells before transplantation of the stem cells, such as autologous stem cell transplantation typically performed in conjunction with high dose chemotherapy.

In addition, PRLR are expressed on cells of the immune system (Clevenger et al., J Endocrinol 157, 187-197 (1998); Pellegrini et al., Mol Endocrinol 6, 1023-1031 (1992)), including circulating T cells. Consistent with this finding, PRLR has also been reported to be expressed on the JURKAT human T cell leukemia line. Anti-PRLR mAbs may thus be used as immune modulators.

For therapeutic applications, the anti-PRLR antibody can be administered alone or in combination with other forms of conventional therapy, either consecutively with, pre- or post-conventional therapy. Currently, depending on the stage of the cancer, breast cancer treatment involves one or a combination of the following therapies: surgery, radiation therapy, hormonal therapy, and chemotherapy. Anti-PRLR antibody therapy may be especially desirable in elderly patients who do not tolerate the toxicity and side effects of chemotherapy well, and in metastatic disease where radiation therapy has limited use.

The anti-PRLR antibody can be administered with a therapeutically effective dose of at least one chemotherapeutic agent or a cocktail of chemotherapeutic agents. Cancer cells are known to deregulate cell survival signaling pathways by increasing the cell survival signals that enter a cell. In turn, enhanced cell survival signaling is known to confer resistance to chemotherapeutic drugs. Therefore, inhibition of cell survival signaling pathway would be expected to enhance the effectiveness of any standard-of-care chemotherapeutic drug for any cancer indication. Therefore, it is contemplated that the anti-PRLR antibodies that inhibit cell survival signaling pathway (e.g., AKT, see Example 4) will increase the sensitivity of cancer cells to chemotherapeutic agents.

Examples of chemotherapeutic agents include, without being limited to, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin 2 (including recombinant interleukin 2, or rIL2), interferon (such as interferon α-2a; interferon α-2b; interferon α-n1; interferon α-n3; interferon β-1a; interferon γ-1b); iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Chemotherapeutic agents and biologics also include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; β-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte α interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase;

metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+ pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; $O_6$-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Examples of therapeutic antibodies that can be used include but are not limited to HERCEPTIN® (Trastuzumab) (Genentech, Calif.), which is a humanized anti-HER2 monoclonal antibody for the treatment of patients with metastatic breast cancer; REOPRO® (abciximab) (Centocor), which is an anti-glycoprotein IIb/IIIa receptor on the platelets for the prevention of clot formation; ZENAPAX® (daclizumab) (Roche Pharmaceuticals, Switzerland), which is an immunosuppressive, humanized anti-CD25 monoclonal antibody for the prevention of acute renal allograft rejection; PANOREX™, which is a murine anti-17-IA cell surface antigen IgG2a antibody (Glaxo Wellcome/Centocor); BEC2, which is a murine anti-idiotype (GD3 epitope) IgG antibody (ImClone System); IMC-C225, which is a chimeric anti-EGFR IgG antibody (ImClone System); VITAXIN™, which is a humanized anti-αVβ3 integrin antibody (Applied Molecular Evolution/MedImnune); Campath 1H/LDP-03, which is a humanized anti CD52 $IgG_1$ antibody (Leukosite); Smart M195, which is a humanized anti-CD33 IgG antibody (Protein Design Lab/Kanebo); RITUXAN™, which is a chimeric anti-CD20 IgG1 antibody (IDEC Pharm/Genentech, Roche/Zettyaku); LYMPHOCIDE™, which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G.1 is a humanized anti-complement factor 5 (C5) antibody (Alexion Pharm); D2E7 is a humanized anti-TNF-α antibody (CAT/BASF); CDP870 is a humanized anti-TNF-α. Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptavidin (+biotin-yttrium 90; NeoRx); CDP571 is a humanized anti-TNF-α $IgG_4$ antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-1 52 is a human anti-TGF-$\beta_2$ antibody (Cambridge Ab Tech).

The Physicians' Desk Reference (PDR) discloses dosages of chemotherapeutic agents that have been used in treatment of various cancers. The dosing regimen and dosages of chemotherapeutic agents that are therapeutically effective will depend on the particular cancer being treated, the extent of the disease and other factors familiar to the physician of skill in the art and can be determined by the physician. As discussed above, it is contemplated that anti-PRLR antibodies will sensitize cancer cells to chemotherapeutic agents. Therefore, it is contemplated that a lower dose of chemotherapeutic agents will be required when combined with anti-PRLR antibodies.

In one particular embodiment, an immunoconjugate comprising the anti-PRLR antibody conjugated with a cytotoxic agent is administered to the patient. Preferably, the immunoconjugate bound to the PRLR protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The anti-PRLR antibodies or immunoconjugates are administered to a subject in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

It may also be desirable to combine the anti-PRLR antibodies with an antibody directed against another epitope of PRLR or another target associated with the particular cancer. For example, since C7, 3E8, 2G5, C8 and G3 recognize different epitopes in the human PRLR, they can be used in combination. Hercepting, which recognizes a different target in breast cancer therapy, can also be used in combination with the anti-PRLR antibodies.

The antibody may be combined with an anti-hormonal compound; e.g., an anti-estrogen compound such as tamoxifen; an anti-progesterone such as onapristone; or an anti-androgen such as flutamide, in dosages known for such molecules. Where the cancer to be treated is estrogen independent cancer, the patient may previously have been subjected to anti-estrogen therapy and, after the cancer becomes estrogen independent, the anti-PRLR antibody (and optionally other agents as described herein) may be administered to the patient.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy as a way to deliver the antibody. There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient. There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fuision, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex 1 virus, or adeno-associated virus) and lipid-based systems (e.g., DOTMA, DOPE and DC-Chol).

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| ° C. = | degree Celsius |
| hr = | hour |
| min = | minute |
| sec = | second |
| µM = | micromolar |
| mM = | millimolar |
| M = | molar |
| ml = | milliliter |
| µl = | microliter |
| mg = | milligram |
| µg = | microgram |
| PBS = | phosphate buffered saline |
| PE = | phycoerythrin |
| PRL = | prolactin |
| PRLR = | prolactin receptor |

Materials and Methods

Expression and Purification of PRLR-Fc Fusion Protein for Immunization and Screening:

An expression plasmid was constructed to express a PRLR-Fc fusion protein (see FIG. 1). The fusion protein contains the extracellular portion of the human prolactin receptor at the N-terminus, followed by a tev (Tobacco Etch Virus) cleavage site, fused to the human IgG, Fc domain. This PRLR-Fc fusion protein was expressed in HEK.EBNA cells according to standard protocols, and purified from the supernatant of the transfected cells by standard protein-A affinity column purification (Harlow and Lane, Antibodies, A Laboratory Manual. Cold Spring Harbor Laboratory, 1988). Briefly, the supernatant was passed through a protein A affinity column and eluted in a low pH buffer (100 mM sodium phosphate, pH 2.8), and dialyzed in PBS. The protein was characterized by SDS-PAGE, N-terminal sequencing and mass spectroscopy analysis. These methods revealed a single protein product of the expected size and mass with >95% purity. This PRLR-Fc fusion protein was also used for the ELISA assay.

The N-terminal PRLR extracellular domain was cleaved for immunization in mice, by cleaving the PRLR-Fc fusion protein with the TEV (Tobacco Etch Virus) protease according to a standard protocol (Haspel et al., Biotechniques 30, 60-61, 64-66 (2001)).

Antibody Purification:

Monoclonal antibodies were purified from hybridoma supernatants by standard protein A affinity chromatography (Harlow and Lane, Antibodies, A Laboratory Manual. Cold Spring Harbor Laboratory, 1988) for use in ELISA, FACS and cell-based signaling and proliferation assays.

ELISA Assay to Identify Antibodies that Bind PRLR:

Antibodies were tested for binding to recombinant prolactin receptor (PRLR-Fc fusion protein, FIG. 1) using a standard ELISA assay. Briefly, the PRLR-Fc fusion protein was coated onto 96-well plates at 5 μg/ml in PBS overnight. The plates were rinsed and incubated with candidate antibodies in PBS containing 0.05% Tween-20 and 1% BSA for one hour at room temperature. The plates were washed, and the amount of bound antibodies was determined with goat anti-mouse IgG HRP conjugate.

FACS Assay to Show Antibody Binding and Specificity:

Following isolation of hybridoma clones that recognized PRLR-Fc fusion protein by the ELISA assay, purified antibodies were tested for their ability to recognize PRLR protein on the surface of various cell lines by FACS. Briefly, cells were grown under standard tissue culture conditions. For the transient expression in 293T cells, the expression constructs were transiently transfected into the cells using Fugene (Roche) and analyzed 36 hr post-transfection.

The cells were harvested by washing in PBS and incubating in PBS plus 5 mM EDTA for 5 minutes. Cells are resuspended in FACS buffer (0.1% BSA in PBS) on ice, counted, and $1 \times 10^6$ cells were placed in each well of a 96-well plate. The cells were spun and resuspended in 150 ul FACS buffer containing 5 ug/ml antibody. For all experiments, the MOPC-21 $IgG_1$ control antibody (BD Biosciences) was used as a negative control. After a 20-minute incubation on ice, cells were spun and resuspended in FACS buffer containing the secondary antibody, goat anti-mouse PE (Jackson ImrunoResearch), and incubated for 20 minutes. The cells were then washed twice in FACS buffer, fixed in 1% paraformaldehyde, and analyzed by FACS.

Binding Studies Using BIAcore Chips:

A BIAcore 2000™ biosensor system (BIAcore, Inc.) was used to study the binding of various mAbs to immobilized PRLR-Fc, and their effects on PRL binding to the same receptor. All experiments were performed at 25° C. with a 10 μl/minute flow rate, using HBS buffer (10 mM HEPES, 150 mM NaCl, 3.4 mM EDTA, 0.005% P20 surfactant, at pH 7.4). The same solution was used both as running buffer and as sample diluent.

The CM5 chip (BIAcore, Inc.) surface was first activated with N-hydroxysuccinimide/N-ethyl-N'-(3-diethylaminopropyl)-carbodiimide hydrochloride (BIAcore, Inc.). PRLR-Fc, diluted to 30 μg/ml in 10 mM acetic acid (pH 5), was then injected. The un-reacted groups of the chip's dextran matrix were then blocked once with 30 μl and again with 15 μl of ethanolamine-HCl (pH 8.5). The chip was regenerated with a 20 μl injection of 1 mM formic acid, repeated five times to establish a reproducible and stable baseline.

For the experiment, anti-PRLR mAbs and PRL were diluted to 30 μg/ml in diluent buffer. For each run, 100 μl of one of the anti-PRLR-Fc mAbs was injected over the surface of the chip followed by a 100 μl injection of PRL over the PRLR-Fc/anti-PRLR-Fc mAb complex. Immediately after each injection, the chip was washed with 300 μl of the diluent buffer. The surface was regenerated between experiments by injecting 20 μl of 1 mM formic acid, followed by a 15 μl injection of lmM formic acid and then a 10 μl injection of lmM formic acid. After regeneration, the chip was equilibrated with the diluent buffer.

FACS Assay to Determine the Functional Affinities of PRLR Antibodies:

BT474 human breast cancer cells were grown in RPMI plus 10% FBS. The cells were detached from culture flasks with PBS containing 20 mM EDTA at room temperature for 5 minutes. The resulting suspension was centrifuged, the cells resuspended in PBS, and the cell suspension was added to antibodies at various concentrations in a 96-well polypropylene plate. After a one-hour incubation at 4° C., the cells were washed three times in PBS and incubated with a 1:500 dilution of anti-mouse IgG phycoerythrin for one hour at 4° C. The cells were then washed once and analyzed by flow cytometry. The mean fluorescence intensity (MFI) was plotted against antibody concentration, and the resulting curve was fit using a four-parameter equation using DeltaGraph software. If no saturation was reached in the binding experiments, an approximate value for the affinity is determined by estimating maximum binding based on the maximum MFI of the other antibodies.

Identification of Epitope Groups for the Antibodies:

The antibodies were sorted into epitope groups by competition ELISA. All antibodies were conjugated with biotin (using a biotin XX linker kit from Molecular Probes) and tested for binding to purified PRLR-Fc fusion protein. Each antibody was then tested against another, unconjugated antibody to allow competition for the fusion protein. All antibodies blocked their own corresponding conjugated forms, but none of the antibodies blocked the others.

Cell Signaling Assay:

T-47D cells were plated onto 60 mm tissue culture dishes in media containing 10% FBS at ~70% confluency (~$0.8 \times 10^6$ cells/plate). The cells were allowed to adhere for 4-6 hr before switching the media to identical media that lack serum, and incubated overnight. The following day PRL ligand (R&D Systems) was added at a concentration of 0.1 ug/ml and incubated for 15 min. A Stop Buffer (PBS containing 0.4 mM NaOrthovanadate) was then added, and the cells were scraped and harvested into test tubes on ice. Cells were then spun briefly in a centrifuge and the supernatant was removed. 40 ul of a Lysis Buffer (10 mM Tris, pH 7.5, 5 mM EDTA, 150 mM NaCl, 10% glycerol, 0.5% Triton X-100, Roche complete protease inhibitor cocktail, 50 mM NaF, 30 mM Na Phosphate, 1 mM NaOrthovanadate) was then added to the cell pellet. 50 ug total cell lysate was analyzed by SDS-PAGE and immunoblotting was performed with the following antibodies: Phosho STAT5 A/B Y694/Y699 (Upstate), Phospho AKT and total AKT (Cell Signaling PhosphoPlus AKT Ser 473 Kit), and Phospho MAPK (PhosphoPlus p44/42 MAPK Thr202/Tyr204 Kit).

Cell Proliferation Assay:

T-47D human breast cancer cells (ATCC) were plated in 96-well plates in a culture medium plus 10% FBS on Day 1 at 10,000 cells/well. This medium was changed to a medium containing 2% charcoal stripped serum for an overnight incubation. On Day 2, cells were treated with 5 ug/ml PRLR antibodies or the MOPC control antibody (BD Biosciences) for 2 hours, followed by 0.1 ug/ml PRL ligand (R&D Systems). On Day 3, cells were again treated with the antibody and the ligand at the same time. Cell proliferation was measured by $H^3$-thymidine incorporation on Day 4.

Pharmacokinetic (PK) Analysis of Antibodies:

PK analysis was performed by injecting 1 mg/kg each antibody intraperitoneally (i.p.) into female athymic nude mice. Blood samples were taken at the following time points following injection (3 mice per time point): 15 min, 30 min, 1 hr, 2 hr, 6 hr, 24 hr, 48 hr, 96 hr, 168 hr, 216 hr, 264 hr, and 336 hr.

Example 1

Production and Affinities of PRLR Specific Antibodies

To generate monoclonal antibodies against the human PRLR, the PRLR extracellular domain of the expected mature sequence (amino acid residues 25-238 of the nascent PRLR protein) was fused to the human IgG$_1$ Fc domain. A 7-amino acid protease cleavage site was inserted in between so that the TEV protease (Tobacco Etch Virus) can be used to release the PRLR extracellular domain from the fusion protein. The fusion protein (see FIG. 1) was expressed and purified, and used to raise monoclonal antibodies as described in Materials and Methods.

The resulting hybriodoma clones were screened for their binding activities to the fusion protein by ELISA as described in Materials and Methods. Five hybridomas were chosen for further analyses. These mAbs produced by these hybridomas all recognize human PRLR on the cell surface of intact cells as shown in FACS analyses. Thus, PRLR-positive T-47D or MCF-7 human breast cancer cells were used to bind each of these mAbs, followed by fluorescence-labeled secondary antibodies that recognize the mAbs. The cells were then analyzed by FACS. As shown in FIG. 2, the mAbs were capable of binding both T-47D (FIG. 2A) and MCF-7 cells (FIG. 2B). In contrast, the control MOPC-21 antibody did not bind either T-47D or MCF-7 cells.

These five hybridomas have high binding affinities for human PRLR, with affinities around the nM level. When the antibodies were allowed to compete with one another in pairs in order to determine if they bind to the same epitope (see Materials and Methods), none of the antibodies competed with another. Therefore, each of the antibodies belongs to a different epitope group, arbitrarily assigned as Group A, B, C, D, or E. These characteristics are shown in Table 2 below. The "fuision partner" indicates the fusion partner in the cell fusion step during hybridoma preparation.

TABLE 2

Affinities of the PRLR antibodies

| Clone name | Abbreviated name | Fusion partner | Functional Affinity (nM) | Epitope Group |
|---|---|---|---|---|
| 4P1E9.C7 | C7 | SP2/0 | 2.52 | A |
| 4P1B3.3E8 | 3E8 | SP2/0 | 0.1 | B |
| 4P1E5.2G5 | 2G5 | SP2/0 | 0.173 | C |
| 4P4F1.C8 | C8 | FL653 | ~13 | D |
| 4P4H6.G3 | G3 | FL653 | ~13 | E |

Example 2

The PRLR Antibodies Specifically Recognize Human PRLR

The five PRLR mAbs were tested for their abilities to recognize human and mouse PRLR by FACS analyses using 4 different cell populations: A) 293T human kidney cells transiently transfected with a human PRLR expression construct, B) 293T cells transiently transfected with a mouse PRLR expression construct, C) PRLR-positive MX-1 human breast cancer cells, and D) PRLR-positive HC-11 mouse mammary epithelial cells.

The results (FIG. 3) show that, as expected, the PRLR mAbs recognized the 293T cells transiently transfected with human PRLR and the MX-1 cells. However, they were unable to recognize the 293T cells transiently transfected with mouse PRLR, or the HC11 mouse cells. Therefore, all five mAbs are specific for the human PRLR.

Example 3

The Antibodies Inhibit PRL Binding to PRLR

To determine if the antibodies block the binding between PRL and PRLR, the BIAcore biosensor system was used as described in Materials and Methods. Briefly, the PRLR-Fc fusion protein was immobilized to the BIAcore chip, and a test mAb was allowed to bind to the immobilized PRLR. Subsequently, PRL was added to the chip. Binding of the antibodies and PRL to the chip was continuously monitored during the course of the experiments. The results indicate that 3E8, 2G5, C8 and G3, but not C7, all blocked binding of PRL to PRLR.

Example 4

The Antibodies Inhibit PRL Signaling

Upon binding to its ligand PRL, PRLR signals through the JAK/STAT and Ras pathways to exert its various functions, including milk production, cell proliferation, and cell survival. More specifically, activation of JAK2 and STAT5 via phosphorylation leads to increased transcription of the milk protein gene β-casein. Activation of the Ras pathways activates, in turn, downstream effectors MAPK and AKT via phosphorylation of those proteins. Activation of MAPK typically enhances cell proliferation, and activation of AKT is known to enhance cell survival.

To determine if the five mAbs can inhibit PRL signaling, T-47D cells were treated with PRL and candidate mAbs as described in Materials and Methods. Cell lysates were then prepared from the treated cells and used in Western blot analyses with antibodies that detect phosho STAT5, phospho AKT, and phospho MAPK, respectively. Anti-total AKT antibodies were also employed as a loading control. The results are shown in FIG. 4. With the exception of C7, the mAbs significantly inhibited phophorylation of STAT, AKT and MAPK. The negative control antibody, MOPC, had no effects. These results are consistent with those from EXAMPLE 3, and indicate that the four inhibitory antibodies can be used to inhibit phosphorylation of these effectors triggered by PRL.

Example 5

The Antibodies Inhibit Breast Cancer Cell Proliferation

To determine whether the mAbs inhibit breast cancer cell proliferation, T-47D cells were incubated with PRL and candidate antibodies in the presence of $H^3$-thymidine, as described in Materials and Methods. A few days later, the cells were harvested and $H^3$-thymidine incorporation measured. As shown in FIG. 5 and summarized in Table 3, 3E8, C8 and G3 significantly inhibited T-47D cell proliferation. 2G5 was not as effective as 3E8, C8 and G3 in inhibiting PRL signaling, and it did not significantly inhibit T-47D cell proliferation. C7 and the control antibody MOPC, which did not inhibit PRL signaling, had no effect on PRL-induced T-47D cell proliferation. These results thus indicate that 3E8, C8 and G3 are the most useful among the 5 mAbs in reducing tumor cell proliferation.

TABLE 3

Summary of signaling-blocking and anti-proliferative activities of PRLR mAbs

| Clone name | Abbreviated name | Block MAPK Signaling | Block AKT Signaling | Block STAT5 Signaling | Block T-47D cell proliferation |
|---|---|---|---|---|---|
| 4P1E9.C7 | C7 | − | − | − | − |
| 4P1B3.3E8 | 3E8 | +++ | +++ | +++ | +++ |
| 4P1E5.2G5 | 2G5 | ++ | ++ | ++ | − |
| 4P4F1.C8 | C8 | +++ | +++ | +++ | +++ |
| 4P4H6.G3 | G3 | +++ | +++ | +++ | +++ |

Example 6

Pharmacokinetic (PK) Analysis of the Antibodies

PK analysis was performed as described in Materials and Methods. The resulting PK statistics are shown in Table 4. AUCinf indicates area under the curve to infinity, CL/F indicates clearance, t1/2 indicates half-life in serum, Cmax indicates maximal concentration, T max indicates time to reach maximal concentration and Vdz/F indicates the volume of distribution.

TABLE 4

Pharmacokinetic (PK) Parameters of antibodies in female athymic nude mice

| PK Parameters | Unit | 4P1E9.C7 | 4P1B3.3E8 | 4P1E5.2G5 | 4P4F1.C8 | 4P4H6.G3 |
|---|---|---|---|---|---|---|
| AUCinf | day*ug/mL | 128.82 | 118.57 | 168.91 | 133.90 | 141.36 |
| CL/F | mL/day/kg | 7.76 | 8.43 | 5.92 | 7.47 | 7.07 |
| t½ | day | 8.51 | 11.18 | 9.98 | 8.19 | 10.26 |
| Cmax | mL/day/kg | 9.21 | 11.10 | 11.46 | 10.62 | 9.92 |
| Tmax | day | 4.00 | 0.25 | 1.00 | 1.00 | 0.25 |
| Vdz/F | mL/kg | 95.33 | 136.00 | 85.21 | 88.24 | 104.76 |

Accordingly, the antibodies all had a quite long half-life and, except C7, reached maximal concentrations rather quickly.

A number of embodiments of the invention have been described. Nevertheless, it will be understood that various modifications may be made without departing from the spirit and scope of the invention.

All of the publications, patents and patent applications cited in this application are herein incorporated by reference in their entirety to the same extent as if the disclosure of each individual publication, patent application or patent was specifically and individually indicated to be incorporated by reference in its entirety.

---

What is claimed is:

1. A hybridoma deposited at the American Type Culture Collection (ATCC) as PTA-6480.

2. An isolated antibody produced by the hybridoma of claim 1, wherein the antibody binds the human prolactin receptor.

3. A humanized or chimeric antibody comprising each of the six CDRs of the heavy and light chain of the isolated antibody of claim 2, wherein the humanized or chimeric antibody binds the human prolactin receptor.

4. A composition comprising the antibody of claim 2.

5. The composition of claim 4 further comprising a chemotherapeutic agent.

6. The composition of claim 4 further comprising an additional antibody.

7. The composition of claim 6 wherein the additional antibody recognizes the human prolactin receptor.

8. An Fab fragment, Fab' fragment, F(ab')2 fragment or Fv fragment of the isolated antibody of claim 2.

9. A single chain antibody comprising the variable heavy chain domain and the variable light chain domain of the isolated antibody of claim 2.

10. The humanized or chimeric antibody of claim 3 comprising a detectable label.

11. The Fab fragment, Fab' fragment, F(ab')2 fragment or Fv fragment of claim 8 comprising a detectable label.

12. The single chain antibody of claim 9 comprising a detectable label.

13. The isolated antibody of claim 2, wherein said antibody is conjugated to a detectable label.

* * * * *

SEQUENCE LISTING

```
<160> NUMBER OF SEQ ID NOS: 1

<210> SEQ ID NO 1
<211> LENGTH: 448
<212> TYPE: PRT
<213> ORGANISM: Artificial Sequence
<220> FEATURE:
<223> OTHER INFORMATION: Synthetic construct

<400> SEQUENCE: 1

Gln Leu Pro Pro Gly Lys Pro Glu Ile Phe Lys Cys Arg Ser Pro Asn
 1               5                  10                  15

Lys Glu Thr Phe Thr Cys Trp Trp Arg Pro Gly Thr Asp Gly Gly Leu
            20                  25                  30
```

-continued

```
Pro Thr Asn Tyr Ser Leu Thr Tyr His Arg Glu Gly Glu Thr Leu Met
         35                  40                  45

His Glu Cys Pro Asp Tyr Ile Thr Gly Gly Pro Asn Ser Cys His Phe
 50                  55                  60

Gly Lys Gln Tyr Thr Ser Met Trp Arg Thr Tyr Ile Met Met Val Asn
 65                  70                  75                  80

Ala Thr Asn Gln Met Gly Ser Ser Phe Ser Asp Glu Leu Tyr Val Asp
                 85                  90                  95

Val Thr Tyr Ile Val Gln Pro Asp Pro Leu Glu Leu Ala Val Glu
                100                 105                 110

Val Lys Gln Pro Glu Asp Arg Lys Pro Tyr Leu Trp Ile Lys Trp Ser
            115                 120                 125

Pro Pro Thr Leu Ile Asp Leu Lys Thr Gly Trp Phe Thr Leu Leu Tyr
        130                 135                 140

Glu Ile Arg Leu Lys Pro Glu Lys Ala Ala Glu Trp Glu Ile His Phe
145                 150                 155                 160

Ala Gly Gln Gln Thr Glu Phe Lys Ile Leu Ser Leu His Pro Gly Gln
                165                 170                 175

Lys Tyr Leu Val Gln Val Arg Cys Lys Pro Asp His Gly Tyr Trp Ser
            180                 185                 190

Ala Trp Ser Pro Ala Thr Phe Ile Gln Ile Pro Ser Asp Phe Thr Met
        195                 200                 205

Asn Asp Thr Thr Val Trp Glu Asn Leu Tyr Phe Gln Gly Val Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```